(12) United States Patent
Oyama et al.

(10) Patent No.: US 11,064,891 B2
(45) Date of Patent: Jul. 20, 2021

(54) OBJECT INFORMATION ACQUIRING APPARATUS

(71) Applicant: CANON KABUSHIKI KAISHA, Tokyo (JP)

(72) Inventors: Kenji Oyama, Tokyo (JP); Robert A Kruger, Oriental, NC (US)

(73) Assignee: CANON KABUSHIKI KAISHA, Tokyo (JP)

( * ) Notice: Subject to any disclaimer, the term of this patent is extended or adjusted under 35 U.S.C. 154(b) by 801 days.

(21) Appl. No.: 14/838,875

(22) Filed: Aug. 28, 2015

(65) Prior Publication Data

US 2016/0066792 A1   Mar. 10, 2016

Related U.S. Application Data

(60) Provisional application No. 62/046,339, filed on Sep. 5, 2014.

(51) Int. Cl.
*A61B 5/00* (2006.01)
*A61B 8/00* (2006.01)
*A61B 8/08* (2006.01)

(52) U.S. Cl.
CPC .......... *A61B 5/0095* (2013.01); *A61B 5/4312* (2013.01); *A61B 5/684* (2013.01);
(Continued)

(58) Field of Classification Search
CPC ... A61B 5/0095; A61B 8/4477; A61B 8/5207; A61B 8/4209; A61B 8/406; A61B 8/0825; A61B 5/6823; A61B 5/4312; A61B 5/7217; A61B 5/684; A61B 5/70; A61B 8/58; A61B 8/4281; A61B 2562/0204;
(Continued)

(56) References Cited

U.S. PATENT DOCUMENTS 6,104,942 A     8/2000  Kruger ..................... 600/407
9,986,969 B2 *  6/2018  Call ....................... A61B 8/585
(Continued)

FOREIGN PATENT DOCUMENTS

JP        60-14167 A      1/1985
JP    WO 2012108172 A1 *  8/2012    ........... A61B 5/0095
WO      2014/026185 A1    2/2014

OTHER PUBLICATIONS

Office Action dated May 14, 2019, in counterpart application JP 2015-170244 (8 pages).
(Continued)

*Primary Examiner* — Jason M Ip
(74) *Attorney, Agent, or Firm* — Venable LLP

(57) ABSTRACT

An object information acquiring apparatus employed in the present invention includes: a plurality of transducers that generate an electric signal upon reception of an acoustic wave from a measurement subject; a supporter that supports the plurality of transducers such that directional axes of at least a part of the plurality of transducers are gathered together; a point sound source; means for controlling relative positions of the measurement subject and the supporter; a processor that determines respective distances from the plurality of transducers to a focus position of the measurement subject and generates property information relating to the focus position; and a corrector that determines correction data.

21 Claims, 17 Drawing Sheets

(52) U.S. Cl.
CPC .............. *A61B 5/6823* (2013.01); *A61B 5/70* (2013.01); *A61B 5/7217* (2013.01); *A61B 8/0825* (2013.01); *A61B 8/406* (2013.01); *A61B 8/4209* (2013.01); *A61B 8/4477* (2013.01); *A61B 8/5207* (2013.01); *A61B 5/68* (2013.01); *A61B 8/4281* (2013.01); *A61B 8/58* (2013.01); *A61B 2562/0204* (2013.01); *A61B 2562/04* (2013.01)

(58) Field of Classification Search
CPC .... A61B 5/68; A61B 2562/16; A61B 2562/04
See application file for complete search history.

(56) References Cited

U.S. PATENT DOCUMENTS

| | | | |
|---|---|---|---|
| 2010/0249570 A1* | 9/2010 | Carson ................. | A61B 5/0059 600/407 |
| 2013/0123627 A1 | 5/2013 | Oyama ........................ | 600/442 |

OTHER PUBLICATIONS

Office Action dated Aug. 6, 2019, in counterpart application JP 2015-170244 (8 pages).

* cited by examiner

| Transducer No. | θ | φ | Radius | TGx | TGy | TGz |
|---|---|---|---|---|---|---|
| 1 | 100 | 0 | 100 | 98.4808 | 0 | -17.3648 |
| ⋮ | | | | | | |
| n | $\theta_n$ | $\phi_n$ | $r_n$ | $x_n$ | $y_n$ | $z_n$ |
| n+1 | $\theta_{n+1}$ | $\phi_{n+1}$ | $r_{n+1}$ | $x_{n+1}$ | $y_{n+1}$ | $z_{n+1}$ |
| ⋮ | | | | | | |
| ⋮ | | | | | | |

OBJECT INFORMATION ACQUIRING APPARATUS

BACKGROUND OF THE INVENTION

Field of the Invention

The present invention relates to an object information acquiring apparatus.

Description of the Related Art

A technique known as photoacoustic tomography (PAT) has been proposed as a technique for acquiring function information relating to a living organism using light and ultrasonic waves. When biological tissue is irradiated with pulsed light such as visible light or infrared light, and a light-absorbing material in the interior of the organism, in particular a material such as hemoglobin in blood, absorbs energy from the pulsed light so as to expand momentarily, a photoacoustic wave (typically an ultrasonic wave) is generated. This phenomenon is known as a photoacoustic effect. PAT is a technique for visualizing information relating to biological tissue by measuring the photoacoustic wave.

The information relating to the biological tissue may be an optical energy absorption density distribution, which expresses a density distribution of the light-absorbing material in the organism serving as the generation source of the photoacoustic wave. By visualizing the optical energy absorption density distribution, an image of active angiogenesis caused by cancer tissue can be obtained. Moreover, function information such as an oxygen saturation of the blood can be obtained using a light wavelength dependence of the photoacoustic wave.

Furthermore, in the PAT technique, the light and the ultrasonic wave are used to obtain an image of the organism information, and therefore an image diagnosis can be performed non-invasively and without exposure to radiation, which is highly advantageous in terms of reducing a patient burden. It is therefore anticipated that PAT will be used for breast cancer screening and early diagnosis in place of an X-ray apparatus that cannot easily be used for repeated diagnosis.

U.S. Pat. No. 6,104,942 discloses an apparatus that includes a probe constituted by a plurality of transducers arranged in different positions over a substantially spherical crown shape in order to detect a photoacoustic wave. The apparatus is capable of acquiring object information over a wide range by performing a mechanical scan using the probe. According to the technique described in U.S. Pat. No. 6,104,942, when a substantially spherical crown-shaped probe is used, a solid angle at which the photoacoustic wave is measured relative to the object increases, and therefore the object information can be visualized with a high degree of precision. Moreover, by orienting respective reception directions of the plurality of transducers arranged over the substantially spherical crown shape toward a predetermined region, the predetermined region can be visualized with a high degree of sensitivity.
Patent Literature 1: U.S. Pat. No. 6,104,942

SUMMARY OF THE INVENTION

In a probe formed by arranging a large number of transducers over a substantially spherical crown shape or a substantially spherical zone shape, object information relating to a predetermined region can be visualized with superior sensitivity and precision by gathering together axes exhibiting maximum reception sensitivity of the large number of transducers in the predetermined region. To make full use of this advantage, the arrangement of the large number of transducers is preferably managed with a high degree of precision. Further, an electric signal originating from the acoustic wave emitted by the object is analyzed using a distance from a focus position to the transducers and an acoustic velocity through an acoustic transmission medium. It is therefore important to gain an accurate understanding of positional relationships such as the distance and the angle between the focus position and the transducers.

However, it is difficult to form an ideal curved surface that varies smoothly, such as a substantially spherical crown shape or a substantially spherical zone shape, and it is likewise difficult to mount all of the large number of transducers on the curved surface mechanically with a high degree of precision.

Furthermore, actual positions of the transducers may deviate from design positions not only during manufacture, as described above, but also due to variation over time as the apparatus is used. In other words, temporal variation in the positions of the transducers may occur due to repetitive mechanical operations and so on. To deal with this positional deviation, calibrations are preferably performed periodically to learn the precise positions of the transducers and create correction data. However, measuring the positions of all of the transducers arranged on the curved surface is not easy, and it is therefore difficult to perform position measurement repeatedly at periodic intervals.

The present invention has been designed in consideration of the problems described above, and an object thereof is to acquire highly precise object information using a probe formed by arranging a large number of transducers over a substantially spherical crown shape or a substantially spherical zone shape.

The present invention provides an object information acquiring apparatus comprising:

a plurality of transducers that respectively generate electric signals upon reception of an acoustic wave from a measurement subject;

a supporter that supports said plurality of transducers such that directional axes of at least a part of said plurality of transducers are gathered together;

a position controller capable of controlling relative positions of said measurement subject and said supporter;

a processor that determines respective distances from said plurality of transducers to a focus position of said measurement subject on the basis of information indicating respective positions of said plurality of transducers, and uses said distances to generate property information relating to said focus position of said measurement subject from said electric signals; and a corrector which, when said measurement subject is said point sound source, determines correction data to be applied to said information indicating said respective positions of said plurality of transducers, using respective reception times at which said acoustic wave from said point sound source is received in said plurality of transducers and an acoustic velocity on a path of said acoustic wave.

According to the present invention, highly precise object information can be acquired using a probe formed by arranging a large number of transducers over a substantially spherical crown shape or a substantially spherical zone shape.

Further features of the present invention will become apparent from the following description of exemplary embodiments with reference to the attached drawings.

DESCRIPTION OF THE EMBODIMENTS

Figure 1:
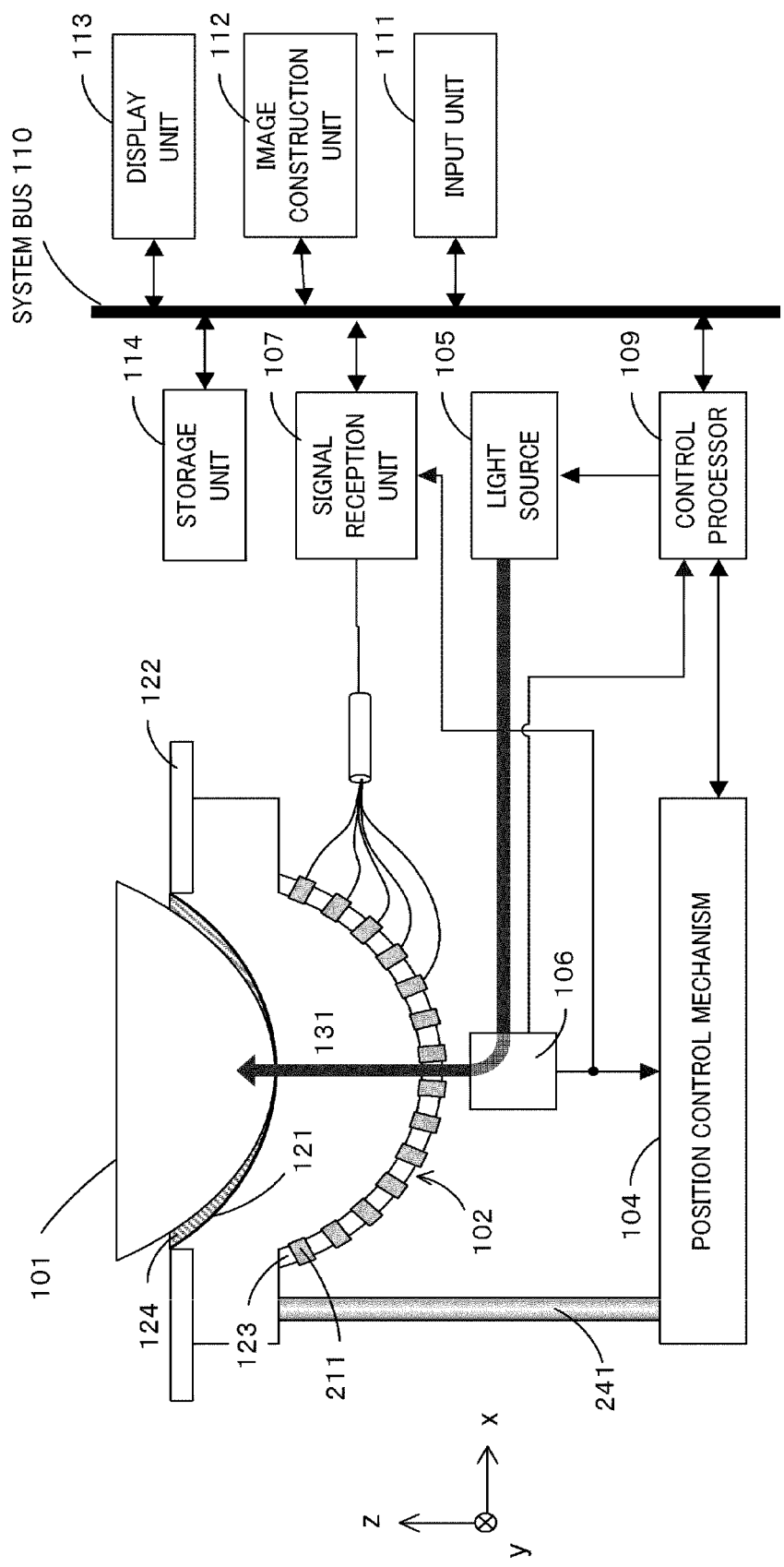
FIG. 1 is a schematic view showing a configuration of an object information acquiring apparatus according to a first embodiment.

Preferred embodiments of the present invention will be described below with reference to the drawings. Note that the scope of the present invention is not limited to the following description, and dimensions, materials, shapes, relative arrangements, and so on of constituent components described below are to be modified appropriately in accordance with a configuration of an apparatus to which the invention is applied and various conditions.

The present invention relates to a technique for generating and acquiring property information relating to an interior of an object by detecting an acoustic wave propagating from the object. The present invention may therefore be considered as an object information acquiring apparatus or a control method thereof, or as an object information acqui- sition method or a signal processing method. The present invention may also be considered as a program for causing an information processing apparatus having a hardware resource such as a CPU to execute these methods, or as a storage medium storing the program. The present invention may further be considered as an acoustic wave measurement apparatus and a control method thereof.

The present invention may be applied to an object information acquiring apparatus that uses a photoacoustic tomography technique for irradiating an object with light (an electromagnetic wave) and receiving (detecting) an acoustic wave that is generated by a photoacoustic effect in a specific position inside or on a surface of the object so as to propagate from the object. This type of apparatus acquires property information relating to the interior of the object in the form of image data, property distribution information, or the like on the basis of photoacoustic measurement, and is therefore known as a photoacoustic imaging apparatus, a photoacoustic image-forming apparatus, or simply a photoacoustic apparatus.

The property information acquired by the photoacoustic apparatus includes a generation source distribution of a photoacoustic wave generated when the object is irradiated with light, an initial sound pressure distribution inside the object, an optical energy absorption density distribution or an absorption coefficient distribution derived from the initial sound pressure distribution, a concentration distribution of a constituent material of tissue, and so on. The material concentration may be an oxygen saturation, an oxyhemoglobin concentration, a deoxyhemoglobin concentration, a total hemoglobin concentration, and so on. The total hemoglobin concentration is a sum of the oxyhemoglobin concentration and the deoxyhemoglobin concentration. Information relating to distributions of fat, collagen, moisture, and so on may also be acquired. Further, the property information may be determined as distribution information relating to respective positions inside the object rather than numerical value data. In other words, distribution information indicating an absorption coefficient distribution, an oxygen saturation distribution, and so on may be acquired as the object information.

The present invention may also be applied to an apparatus that uses an ultrasonic echo technique for acquiring the object information as image data by transmitting an ultrasonic wave to the object and receiving a reflection wave (an echo wave) reflected by the interior of the object. In the case of an apparatus that uses an ultrasonic echo technique, the acquired object information is information reflecting differences in acoustic impedance in the tissue in the interior of the object.

The acoustic wave according to the present invention is typically an ultrasonic wave, but may also be a sound wave or an elastic wave known as an acoustic wave. An acoustic wave generated by the photoacoustic effect is known as a photoacoustic wave or an optical ultrasonic wave. An electric signal (a reception signal) converted from an acoustic wave by a probe is also known as an acoustic signal, and an acoustic signal originating from a photoacoustic wave in particular is known as a photoacoustic signal.

A breast of a living organism may be envisaged as the object according to the present invention. Note, however, that the object is not limited thereto, and another site of a living organism or a material not from a living organism may be examined instead.

The object information acquiring apparatus according to the present invention includes a probe on which a plurality of transducers are arranged. The transducers are configured such that respective axes (directional axes) thereof in a direction exhibiting maximum reception sensitivity are gathered together in at least one predetermined region. By arranging the plurality of transducers in this manner, the probe can receive an acoustic wave generated in the at least one predetermined region in which the directional axes of all or a part of the transducers are gathered together with a high degree of sensitivity.

The object information acquiring apparatus according to the present invention receives an acoustic wave a plurality of times while modifying relative positions of the probe and the object, and stores reception signals output in time series from the probe in a storage medium as signal data. The signal data obtained over several operations in this manner are then used to acquire object information relating to respective focus positions in a region of interest (ROI), or in other words an imaging region.

When the object information acquired in the focus position is visualized from the signal data obtained by receiving acoustic waves using the probe, a resolution is typically highest in at least one predetermined position where the largest number of directional axes of all or a part of the transducers are gathered. The resolution of the object information gradually decreases away from this predetermined position. It is estimated at this time that acoustic waves generated in a predetermined region extending from the predetermined position having the maximum resolution to a point at which the resolution is halved, for example, can be received by the probe with a comparatively high degree of sensitivity. In this specification, therefore, the region extending from the predetermined position having the maximum resolution to the point at which the resolution is halved will be referred to as a "high sensitivity region". In the case of a probe in which a plurality of transducers are supported over a hemispherical shape, for example, the predetermined position in which the largest number of directional axes are gathered corresponds to a curvature center of the hemispherical shape.

First Embodiment

FIG. 1 is a schematic view showing an apparatus configuration of an apparatus according to this embodiment.

(Configuration and Functions of Apparatus)

An object information acquiring apparatus according to this embodiment includes a probe 102, a position controlling mechanism 104, a light source 105, an irradiation optical system 106, a signal receiver 107, a control processor 109, a system bus 110, an input unit 111, an image construction unit 112, a display unit 113, and a storage unit 114.

An object 101 serves as an imaging subject. Specific examples thereof include a living organism such as a breast or a phantom used when adjusting the apparatus or the like to simulate acoustic properties and optical properties of a living organism. Specific examples of the acoustic properties include a propagation velocity and an attenuation rate of an acoustic wave, and specific examples of the optical properties include an absorption coefficient and a scattering coefficient of light. Hemoglobin, water, melanin, collagen, adipose, and so on may be used as a light absorber inside the organism serving as the object. In the phantom, a material that simulates these optical properties is sealed into the interior as the light absorber.

In this embodiment, the object 101 is held by a holder 121. The holder 121 is attached to an attachment portion 122. The attachment portion 122 is configured such that holders 121 having various shapes can be attached thereto interchangeably, and therefore a holder 121 suited to the object 101 can be attached. The holder 121 stabilizes a shape of the breast, and stretches the breast thinly so that light reaches a deep part of the breast. The holder 121 preferably possesses a transmission property relative to light and acoustic waves.

Figure 2A:
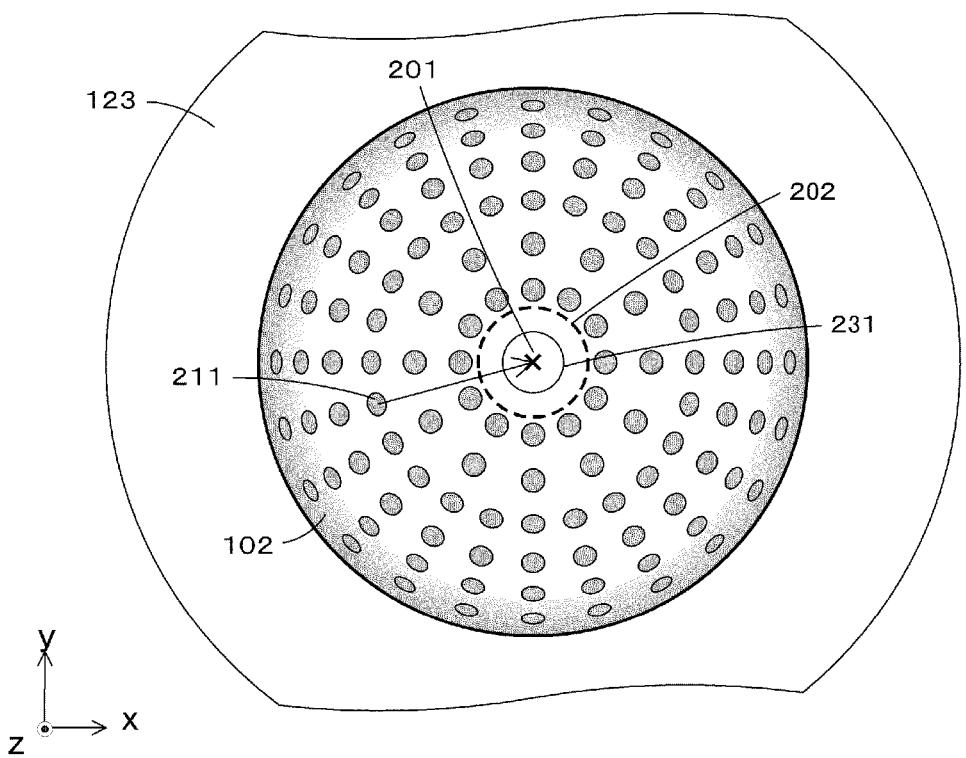
FIGS. 2A and 2B are schematic views showing a configuration of a probe according to the first embodiment.
Figure 2B:
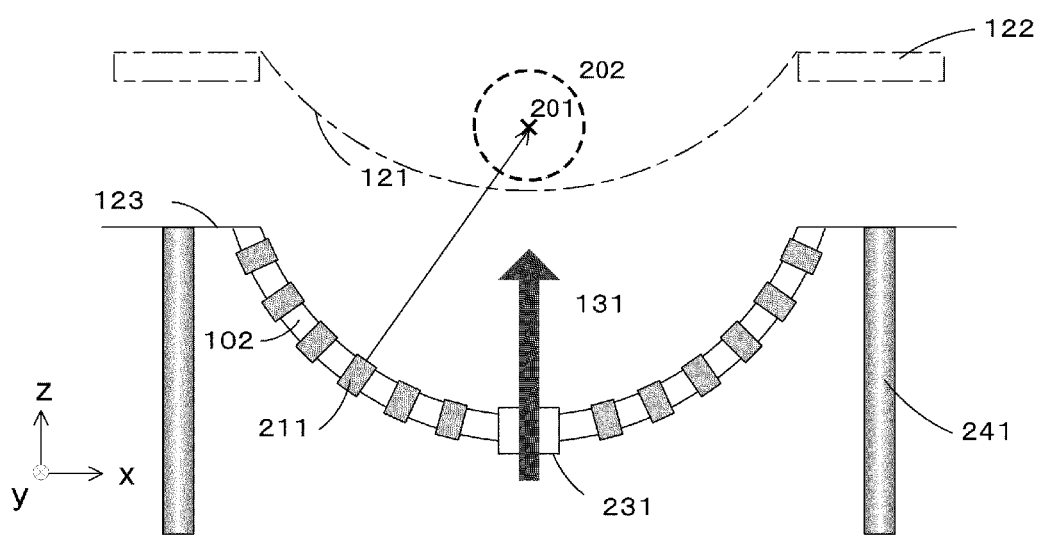

The probe 102 is constituted by a plurality of transducers 211 and a supporter 123 thereof. In this embodiment, as shown in FIG. 2, the supporter 123 takes a substantially hemispherical spherical crown shape, and the plurality of transducers 211 are arranged over the hemispherical shape. FIGS. 2A and 2B are sectional views showing the probe 102 from a z axis direction upper portion and a side face thereof, respectively.

The transducers 211 receive a photoacoustic wave generated in the interior of the object when the object 101 is irradiated with light 131, convert the photoacoustic wave into an electric signal, and output the electric signal as a reception signal. In this embodiment, there are no particular limitations on the type of transducer. A transducer formed using piezoelectric ceramics (PZT) and employed in a typical ultrasonic diagnosis apparatus, for example, may be used. Further, an electrostatic capacitance type CMUT (Capacitive Micromachined Ultrasonic Transducer) or an MMUT (Magnetic MUT) formed using a magnetic film may be used. A PMUT (Piezoelectric MUT) formed using a piezoelectric thin film may also be used.

A point 201 indicates a curvature center point serving as a mechanical design point of the hemispherical surface shape of the supporter 123. The plurality of transducers 211 typically exhibit a maximum reception sensitivity in a normal direction of a reception surface (a front surface) thereof. Accordingly, the plurality of transducers 211 exhibit an effective reception sensitivity within a predetermined angle range centering on the normal direction. This predetermined angle range is set as an orientation angle. By gathering together respective orientation directions of the transducers 211 in the vicinity of the curvature center point 201 of the hemispherical surface shape, a high sensitivity region 202 in which visualization can be achieved with superior sensitivity and precision is formed about the curvature center point 201. Note that by scanning the object 101 with the probe 102 using the position control mechanism 104, or in other words by moving the high sensitivity region 202 relative to the object 101, object information over a wide range can be visualized with superior sensitivity and precision.

Note that in the present invention, the arrangement of the plurality of transducers 211 is not limited to the example of the hemispherical shape shown in FIG. 2, and as long as the directional axes can be gathered together in a predetermined region centering on a mechanical design point such that the predetermined high sensitivity region can be formed, any arrangement may be employed. In other words, the plurality of transducers 211 may be arranged over any curved surface shape as long as the predetermined high sensitivity region is formed. Furthermore, the curved surface according to this specification includes a spherical shape, a hemispherical surface, and other spherical shapes having an opening, such as a spherical crown or a spherical zone. The curved surface according to this specification also includes a surface that includes surface unevenness but may still be considered as a spherical surface, and an ellipsoid that may be considered as a spherical surface (a surface shape obtained by expanding an ellipse in three dimensions such that a surface thereof is constituted by a quadratic surface).

Moreover, in a case where the plurality of transducers are arranged over a spherical crown-shaped or spherical zone-shaped supporter obtained by cutting a sphere along a desired cross-section, the largest number of directional axes are gathered together in the curvature center of the obtained supporter shape. The hemispherical supporter 123 used in the description of this embodiment likewise constitutes an example of a supporter having a shape obtained by cutting a sphere along a desired cross-section.

Figures 3A, 3B:
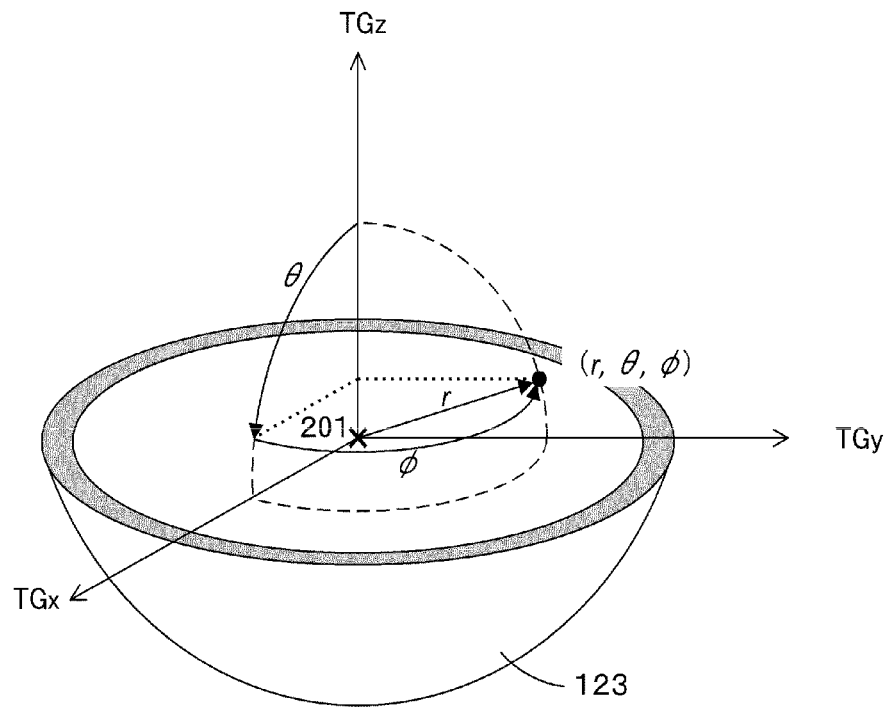
FIGS. 3A and 3B are schematic views showing transducer arrangement data according to the first embodiment.

Furthermore, the arrangement of the plurality of transducers 211 is designed using a spherical coordinate system such as that shown in FIG. 3A, having a radius r, a polar angle $\theta$, and an azimuth $\phi$, and centering on the curvature center point 201 serving as a mechanical design point of the supporter 123. Information indicating the positions of all of the transducers is stored in the storage unit 114 as transducer arrangement data. Note that for ease of description, the coordinate system of the transducer arrangement data will be referred to as a Transducer Geometry coordinate system (TGx, TGy, TGz). The transducer arrangement data are data having a table structure such as that shown in FIG. 3B, in which unique numbers identifying the individual transducers 211 are associated with coordinate values of the spherical coordinate system, for example. In the present invention, correction data for updating or correcting the transducer arrangement data are generated using a method to be described below.

As described above, the plurality of transducers 211 are oriented toward the curvature center point 201. The orientation directions of the transducers 211 can therefore be determined easily on the basis of the information indicating the transducer positions on the same coordinate system. Accordingly, a determination as to whether or not the signal data of the respective transducers 211 contributes to the generation of respective focus positions (pixels or voxels) constituting the object information, which is constituted by two-dimensional or three-dimensional space data, can be made easily using the information indicating the transducer positions on the same coordinate system.

As shown in FIG. 2B, the probe 102 further includes an irradiation hole 231 for guiding the light 131 to a bottom surface thereof. The light 131 guided by the irradiation optical system 106 is emitted in the direction of the high sensitivity region 202 through the irradiation hole 231. Note that an optical system of the present invention may be formed by integrating the irradiation optical system 106 and the irradiation hole 231.

Furthermore, the probe 102 is fixed to the position control mechanism 104 via a connecting portion 241. The position control mechanism 104 is constituted by a drive member such as a motor and a mechanical component for transmitting driving force from the drive member. The movement control mechanism 104 moves a position in which the object 101 is irradiated with the light 131 and a photoacoustic wave reception position by moving the probe 102 in accordance with position control information from the control processor 109. Moreover, it is preferably possible to control the position of the probe 102 in three dimensions (an XYZ space) rather than moving the probe 102 in only two dimensions (an XY plane). With this configuration, the position control mechanism 104 can control relative positions of the supporter (or in other words the respective transducers) and a measurement subject (the point sound source or the object).

By acquiring the signal data repeatedly while moving the position in which the object 101 is irradiated with the light 131 and the position in which the object 101 receives by the probe 102 the photoacoustic wave relative to the object 101, signal data required to generate object information over a wide range can be acquired.

Further, the position control mechanism 104 outputs position data acquired in relation to the probe 102 following emission of the light, or in other words generation of the photoacoustic wave, to the control processor 109 in synchronization with the irradiation control implemented on the light 131 by the irradiation optical system 106. Note that when an ultrasonic wave transmission source is used as the measurement subject, position data acquired in relation to the probe 102 following transmission of the ultrasonic wave are output to the control processor 109 after receiving a synchronization signal transmitted from the ultrasonic wave transmission source, which is constituted by an external apparatus.

The light source 105 emits pulsed light. A pulse width is equal to or smaller than 100 nsec, for example. The light source 105 is typically a solid-state laser capable of emitting pulsed light having a center wavelength in an infrared region. Examples of types of laser include an yttrium-aluminum-garnet laser, a titan-sapphire laser, and so on. Lasers such as a gas laser, a dye laser, and a semiconductor laser may also be used. Moreover, a light-emitting diode or the like may be used instead of a laser.

Note that a wavelength of the light is selected in accordance with the light absorbing material in the organism serving as the measurement subject. The light absorbing material may be, for example, oxyhemoglobin, deoxyhemoglobin, a blood vessel containing large amounts thereof, a malignant tumor containing a large amount of newly formed blood vessels, and so on. Alternatively, the light absorbing material may be glucose, cholesterol, and so on.

When the measurement subject is hemoglobin in a newly formed blood vessel of a breast tumor, light having a wavelength between 600 and 1000 nm is typically absorbed. An amount of light absorbed by water in the organism, on the other hand, reaches a minimum at approximately 830 nm. Between 750 and 850 nm, therefore, the amount of light absorbed by hemoglobin is relatively large. Further, a light absorption rate at each wavelength varies according to the oxygen saturation of the hemoglobin, and therefore functional variation in the organism can be measured using this wavelength dependence property.

The irradiation optical system 106 guides the pulsed light generated by the light source 105 toward the object 101 in order to form and emit the light 131 in a favorable form for acquiring a signal. The irradiation optical system 106 is typically constituted by optical components such as a lens or a prism for condensing or expanding the light, a mirror for reflecting the light, and a diffusion plate for diffusing the light. An optical waveguide such as an optical fiber or the like may also be used to guide the light from the light source 105.

Note that a maximum permissible exposure is defined in IEC60825-1 as a reference relating to irradiation of the skin and eyes with laser light or the like in terms of typical conditions such as the wavelength of the light, the exposure duration, and pulse repetition. The irradiation optical system 106 generates the light 131 so as to satisfy identical conditions in relation to the object 101.

The irradiation optical system 106 preferably further includes an optical configuration (not shown) for detecting emission of the light 131 toward the object 101 and generating a synchronization signal in synchronization therewith in order to control reception and storage of the photoacoustic wave. For example, a part of the pulsed light generated by the light source 105 is separated using an optical system such as a half mirror, whereupon the separated part is guided to an optical sensor. Emission of the light 131 can then be detected using a detection signal generated by the optical sensor. When a fiber bundle is used to guide the pulsed light, emission of the light 131 can be detected by configuring a part of the fiber bundle to branch toward the optical sensor. The synchronization signal generated when emission of the light 131 is detected is input into the signal reception unit 107 and the position control mechanism 104.

The irradiation optical system 106 further includes an optical configuration (not shown) for measuring an energy of the light 131. Data indicating the optical energy are output to the control processor 109 in synchronization with emission of the light 131.

The signal reception unit 107 is constituted by a signal amplifier that amplifies an analog signal generated by the probe 102, an A/D converter that converts an analog reception signal output from the probe 102 into a digital reception signal, and so on. The signal reception unit 107 outputs the generated digital reception signal to the storage unit 114. The storage unit 114 stores the digital reception signal as signal data.

The signal reception unit 107 starts an operation to receive the signal output from the probe 102 using the synchronization signal from the irradiation optical system 106 as a trigger. Note that a delay between input of the synchronization signal and the start of the reception operation can be controlled in relation to each individual transducer or in relation to groups of some of the transducers.

When an ultrasonic wave transmission source is used as the measurement subject, the operation to receive the signal output from the probe 102 is started upon reception of a synchronization signal output from the ultrasonic wave transmission source, which is an external apparatus.

The control processor 109 operates an operating system (OS) that performs basic resource control, management, and so on during a program operation. The control processor 109 reads program code stored in the storage unit 114 in order to execute functions of the embodiments to be described below. Further, the control processor 109 controls various hardware via the system bus 110 upon reception of event notifications generated in response to various operation performed by a user via the input unit 111.

The control processor 109 also functions as a corrector according to the present invention for updating or correcting the transducer arrangement data.

The input unit 111 receives various input from the user (mainly an examiner such as a healthcare professional), and transmits input information to configurations such as the control processor 109 via the system bus 110. For example, the user can use the input unit 111 to set parameters relating to imaging, issue an instruction to start imaging, set observation parameters such as a range and a shape of the region of interest, or in other words the imaging region, perform image processing operations on an image, and so on. The input unit 111 is typically constituted by a mouse, a keyboard, a touch panel, or the like, which is used to issue event notifications to software such as the OS operating on the control processor 109 in response to user operations.

The image construction unit 112 acquires the object information using the signal data stored in the storage unit 114 and data attached thereto, such as the transducer arrangement data. More specifically, the image construction unit 112 converts the signal data, which are time series data, into the object information, which is two-dimensional or three-dimensional space data, on the basis of spatial information such as the three-dimensional positions, orientation directions, and so on of the plurality of transducers 211 included in the transducer arrangement data. When the imaging region is a two-dimensional region, the focus position is a pixel, and when the imaging region is a three-dimensional region, the focus position is a voxel. Furthermore, the image construction unit 112 generates a display image such as a desired tomographic image in accordance with the imaging region.

The image construction unit 112 is typically configured using a GPU (Graphics Processing Unit) or the like having a high-performance calculation processing function and a graphics display function. As a result, an amount of time expended on image reconstruction processing and display image construction can be shortened.

The display unit 113 displays the display image of the object information, generated by the image construction unit 112, a UI for manipulating the image and the apparatus, and so on. Any desired display, such as a liquid crystal display or an organic EL (Electro Luminescence) display, may be used as the display unit 113.

The storage unit 114 includes a volatile or nonvolatile memory required to operate the control processor 109, and a volatile memory that holds data temporarily during the operation to acquire the object information. The storage unit 114 also includes a nonvolatile storage medium such as a hard disk for storing and holding the generated signal data and the data attached to the signal data such as the transducer arrangement data, the visualized object information, and so on. The nonvolatile storage medium serving as the storage unit 114 stores the program code of the software used to realize the functions of the embodiments to be described below.

To form a photoacoustic wave propagation path between the object 101 and the holder 121, an acoustic transmission medium 124 such as water or a gel or gel sheet used for ultrasonic wave measurement is preferably disposed between the object 101 and the holder 121 such that no air gaps are formed.

To form a photoacoustic wave propagation path likewise between the holder 121 and the supporter 123, this space is preferably filled with a medium having high acoustic wave transmission efficiency. The medium also serves as a transmission path of the light 131, and is therefore preferably a material that is transparent to the light 131. Hence, water or the like, for example, is used.

Note that the acoustic transmission medium 124 disposed between the object 101 and the holder 121 may be formed from a different material to the acoustic transmission medium disposed between the holder 121 and the supporter 123.

(Signal Data Acquisition Processing)

Figure 4:
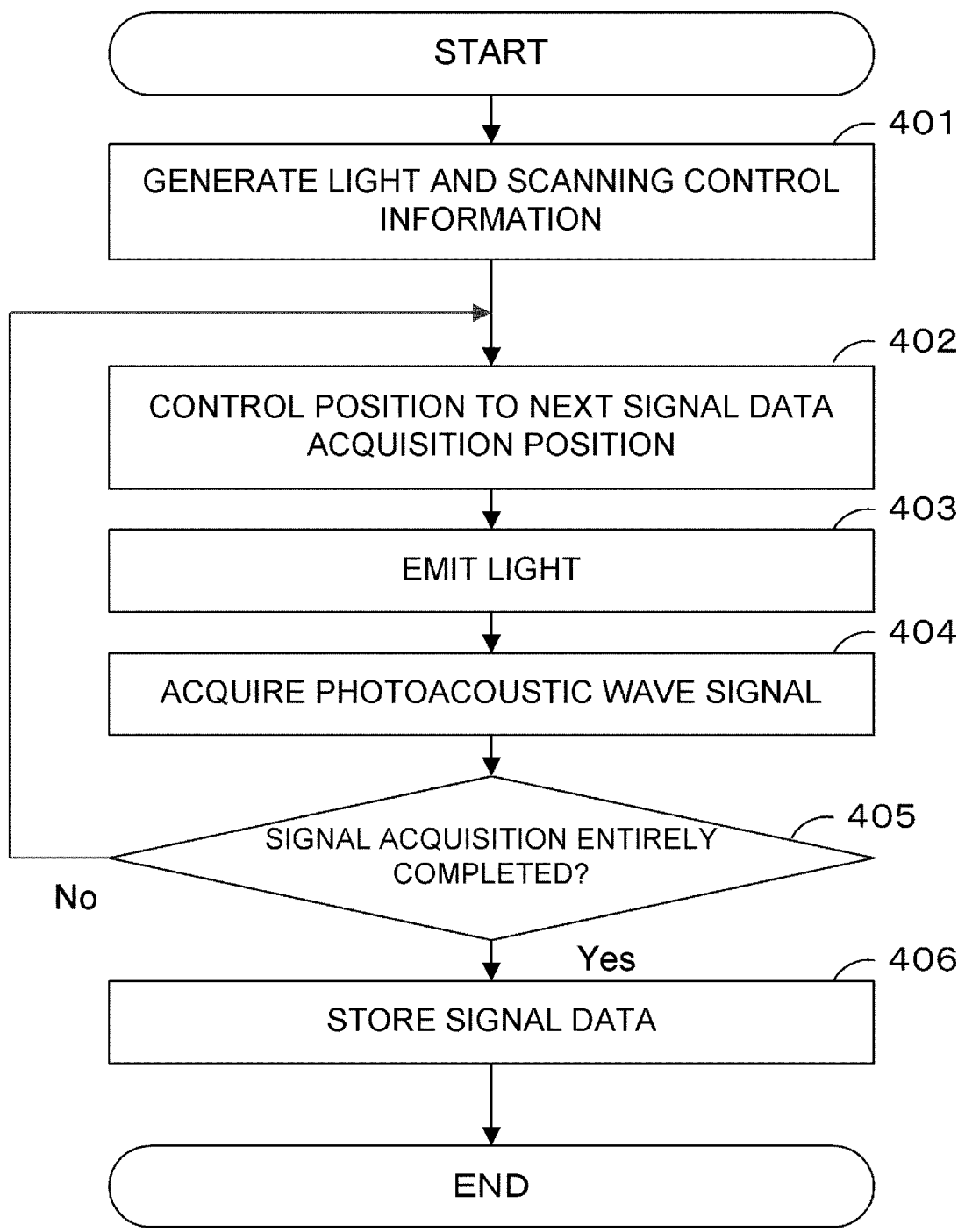
FIG. 4 is a flowchart showing signal data acquisition performed by the object information acquiring apparatus according to the first embodiment.

Referring to FIG. 4, a flow of signal data acquisition performed by the object information acquiring apparatus according to the first embodiment will be described. Here, a series of processes for acquiring property information relating to the interior of the object by measuring the actual object will be described. Note, however, that similar procedures to this flow can be implemented likewise during calibration processing, to be described below, simply by modifying the measurement subject from the object to a point sound source.

In step 401, the control processor 109 generates control information such as the position of the probe 102 and a number of times the light 131 is to be emitted, or in other words a number of times the signal data are to be acquired, in accordance with parameters required to acquire target object information specified by the user via the input unit 111. Further, scanning control can be performed by having the control processor 109 generate control information such as a plurality of position control points on a two-dimensional plane (in the XY plane) or in a three-dimensional space (the XYZ space) and a movement velocity along scanning lines linking the plurality of position control points. The control processor 109 then outputs the control information to the position control mechanism 104, the light source 105, and the signal reception unit 107.

In step 402, the position control mechanism 104 moves the probe 102 to the next position in which the signal data relating to the photoacoustic wave are to be acquired in accordance with the position control information.

In step 403, the light source 105 emits pulsed light in accordance with the emission control information from the control processor 109. The pulsed light emitted from the light source 105 is formed into the light 131 via the irradiation optical system 106, whereupon the light 131 is emitted onto the object 101. The irradiation optical system 106 generates a synchronization signal at the same time as the light 131 is emitted onto the object 101, and transmits the generated synchronization signal to the position control mechanism 104 and the signal reception unit 107.

In step 404, the probe 102 detects a photoacoustic wave generated by and propagated from the object 101 irradiated with the light. Further, the signal reception unit 107 converts the reception signal generated by the probe 102 into a digital signal in synchronization with the synchronization signal input from the irradiation optical signal 106. After receiving the synchronization signal, the signal reception unit 107 receives photoacoustic wave signals in a number corresponding to a predetermined sample number at a predetermined sampling rate. Further, the position control mechanism 104, upon reception of the synchronization signal from the irradiation optical system 106, transmits position data generated in synchronization with emission of the light 131 to the control processor 109.

In step 405, the control processor 109 determines whether or not all of the signal data have been acquired. When all of the signal data have not yet been acquired, the processing advances to step 402, where photoacoustic wave signal acquisition is repeated. When all of the signal data have been acquired, the processing advances to step 406.

In step 406, all of the signal data and attached data acquired by the control processor 109 up to that point are stored in the storage unit 114. The attached data include data indicating the positions of the transducers at the time of signal data acquisition, data indicating the energy of the light 131, the parameters specified by the user, and so on, and also include copies of the transducer arrangement data at the time of signal data acquisition and correction data relating thereto.

(Object Information Acquisition Processing)

Next, referring to FIG. 5, a flow of object information visualization according to the first embodiment will be described.

In step 501, the control processor 109 reads the transducer arrangement data stored together with the signal data at the time of signal data acquisition. When, at this time, correction data exist in relation to the read transducer arrangement data, the control processor 109 corrects the transducer arrangement data using the correction data.

In step 503, the control processor 109 reads the signal data acquired in accordance with the flow shown in FIG. 4 and the data attached thereto, and inputs the read data into the image construction unit 112.

In step 504, the image construction unit 112 forms an image of the object information in the next signal data acquisition position in accordance with the transducer position data serving as the attached data. Note that the object information is data for visualizing property information such as optical property values, and is acquired by performing image reconstruction processing on the signal data. In the present invention, the correction data are applied to the transducer arrangement data used during image reconstruction.

Time domain or field domain back projection, which is typically employed in a tomography technique, phasing addition processing, or the like, for example, is used as the image reconstruction processing. When time constraints are not severe, an image reconstruction method such as an inverse problem analysis method involving repeated processing may also be used.

In step 505, the image construction unit 112 adds the object information visualized in step 504 to a pixel value or a voxel value in consideration of the position within the imaging region. By implementing this process, a plurality of object information generated from signal data acquired individually in different positions can be synthesized. Moreover, an S/N ratio of the finally generated object information can be increased.

In step 506, the image construction unit 112 determines whether or not image-formation and synthesis have been completed on the object information contributing to the imaging region. When image-formation and synthesis are not complete, the processing advances to step 504, where image-formation and synthesis are repeated on the object information in the next signal data acquisition position. When image-formation and synthesis are complete, the processing advances to step 507.

Note that the determination as to whether or not the object information based on the signal data in a single signal data acquisition position contributes to the imaging region can be made by, for example, determining whether or not the high sensitivity region 202 in that signal data acquisition position overlaps the imaging region.

In step 507, the image construction unit 112 generates a display image on the basis of the object information generated up to this step, and notifies the control processor 109 that visualization of the object information is complete. Having received the notification, the control processor 109 displays the display image on the display unit 113. Image display may be implemented using any desired method, but a method that assists an image diagnosis is preferably employed.

Note that in this embodiment, an example in which the object information is visualized in order of the data indicating the positions of the transducers, whereupon the final object information is acquired by synthesizing a plurality of object information, was described. The present invention is not limited to this example, however, and as long as appropriate object information can be acquired using all of the acquired signal data, any method may be used. For example, instead of performing steps 504, 505, and 506 repeatedly, the object information may be acquired in a single visualization process using all of the received signal data at once.

Figure 5:
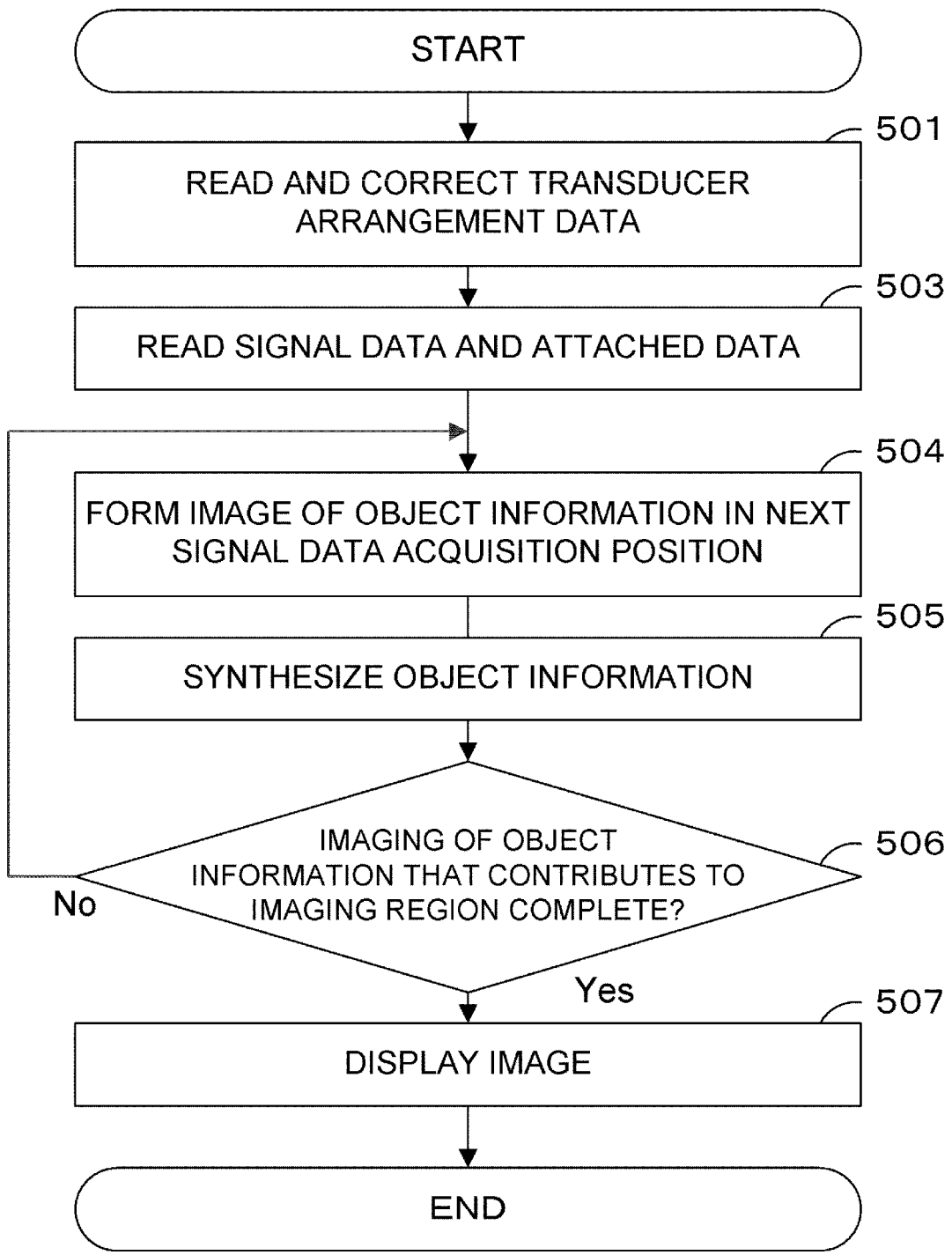
FIG. 5 is a flowchart showing visualization of object information according to the first embodiment.

Meanwhile, acquisition of the signal data and visualization of the object information were described as independent processes using FIG. 4 and FIG. 5, respectively, but since the image reconstruction processing and so on shown in FIG. 5 can be entrusted to the image construction unit 112, or in other words the GPU, this processing may be performed in parallel with the signal data acquisition operation. Hence, by performing step 501 of FIG. 5 before or after step 401 of FIG. 4 and performing steps 502 to 505 between step 404 and step 405, signal data acquisition and visualization of the object information can be implemented in a single integrated flow.

(Data Correction)

Figure 6:
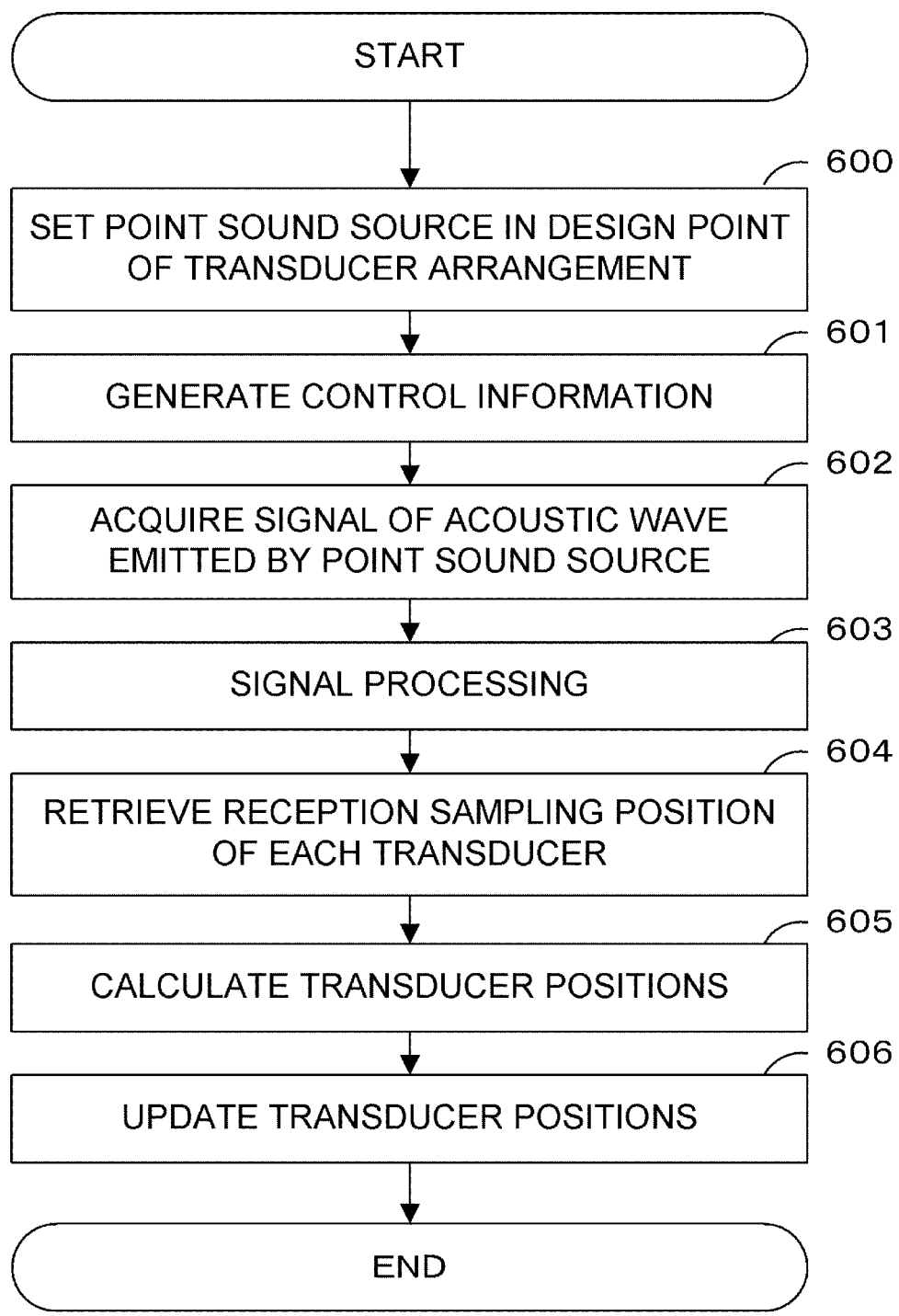
FIG. 6 is a flowchart showing correction according to the first embodiment.

Next, referring to FIG. 6, a flow of correction of the transducer arrangement data according to the first embodiment will be described. This processing is preferably performed during installation of the apparatus, periodically implemented calibrations, and so on. The correction data acquired and stored in this processing are used when generating property information on the basis of the signal data acquired by measuring the actual object. Note, however, that the execution timing of the processing is not limited to these examples.

Figure 7:
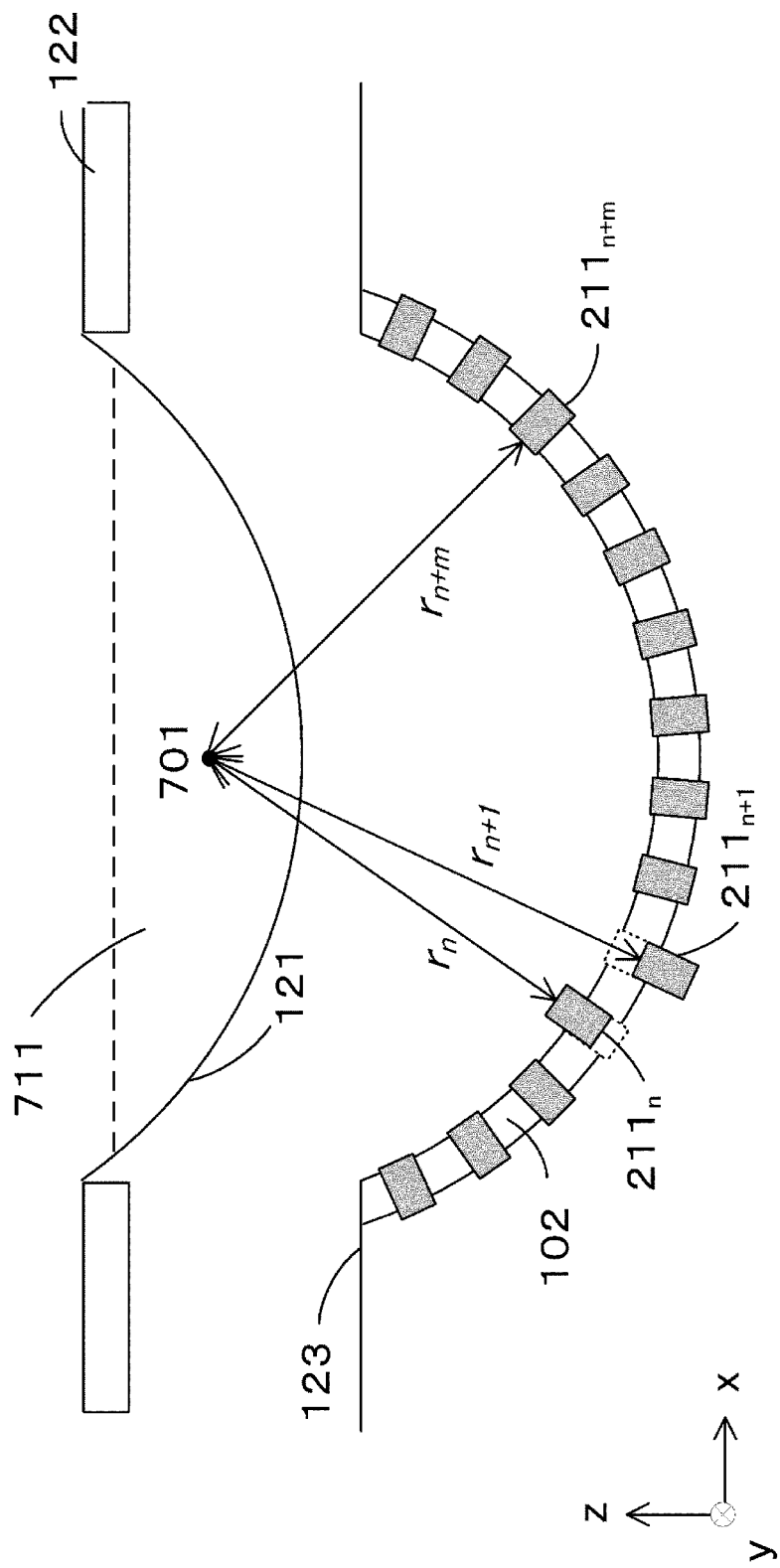
FIG. 7 is a schematic view showing acquisition of signal data used to calculate a correction amount, according to the first embodiment.

In step 600, as shown in FIG. 7, a point sound source 701 is disposed in the curvature center point 201 serving as a mechanical design point of the hemispherical shape of the probe 102. Note that relative positioning between the point sound source 701 and the probe 102 is performed either by having the user adjust the position of the point sound source 701 or by having the position control mechanism 104 adjust the position of the probe 102.

Note that an acoustic transmission medium 711 having a known, stable acoustic velocity property is disposed on an upper portion of the holder 121 at the same time as the point sound source 701 is disposed. More preferably, an identical medium to the acoustic transmission medium used between the holder 121 and the supporter 123 is used. Note that when the curvature center point 201 is designed to be further toward the probe 102 side than the attachment portion 122, the holder 121 may be removed so that the correction is performed using only the acoustic transmission medium provided between the holder 121 and the supporter 123.

In step 601, the control processor 109 generates control information required to acquire signal data used to correct the transducer arrangement data. When a light absorber that emits a photoacoustic wave is used as the point sound source 701, control information for emitting the light 131 at least once is generated.

In step 602, the probe 102 detects an acoustic wave that propagates through the acoustic transmission medium after being emitted by the point sound source 701. Further, the signal reception unit 107 converts the reception signal output from the probe 102 into a digital signal in response to the synchronization signal input from the irradiation optical system 106 or the ultrasonic wave transmission source. After receiving the synchronization signal, the signal reception unit 107 receives photoacoustic wave signals in a number corresponding to the predetermined sample number at the predetermined sample rate, and stores the received signals as signal data.

Note that in this embodiment, the point sound source 701 may be either an ultrasonic wave transmission source or a point-form light absorber that emits a photoacoustic wave. When a light absorber is used, the photoacoustic wave generated when the light 131 is emitted onto the light absorber 701 is detected.

In step 603, the control processor 109 applies a filter having an identical center wavelength to the acoustic wave emitted by the point sound source 701 to the signal data acquired in step 602. As a result, signal components other than those of the acoustic wave originating from the point sound source 701 are removed, leading to an improvement in correction precision.

Further, insteps 601 and 602, signal processing for strengthening the signal components originating from the point sound source 701 may be performed by implementing control such that acoustic wave emission from the point sound source and acquisition of the signal data are performed a plurality of times and the plurality of acquired signal data are integrated. In so doing, the correction precision can be improved.

In step 604, the control processor 109 uses the signal data acquired up to step 603 to retrieve a sampling position of the signal of the acoustic wave emitted by the point sound source 701 in each transducer.

A design distance of each transducer 211 from the curvature center point 201 is known from the mechanical design, and therefore a designed acoustic wave sampling position can be estimated from the design distance and the acoustic velocity of the acoustic transmission medium. By retrieving a sampling position indicating a peak value of the reception signal within a predetermined sampling range centering on the estimated sampling position, a load of the retrieval processing can be lightened.

In step 605, the control processor 109 calculates the distance of a transducer $211_n$ from the point sound source 701, or in other words an actual distance $r_n$ from the curvature center point 201, from a signal data sampling position $S_n$ of the point sound source 701, retrieved in step 604, using Expression (1).

[Math. 1]

$$r_n = cT_n \approx c\frac{S_n}{F} \quad (1)$$

Here, c denotes the acoustic velocity of the acoustic wave through the acoustic transmission medium, $T_n$ denotes a reception time of the acoustic wave, and F denotes the sampling rate of the signal reception unit 107. Note that when a delay is set in the operation of the signal reception unit 107 between input of the synchronization signal and the start of the reception operation, a sample number corresponding to the delay is added to $S_n$.

Actual distances $r_{n+m}$ of transducers $211_{n+m}$ from the curvature center point 201 can be calculated similarly thereafter.

In step 606, the transducer arrangement data stored and held in the storage unit 114 are updated using the actual distances of the plurality of transducers 211 from the curvature center point 201, calculated in step 605. In other words, the values of the data shown in FIG. 3B are updated. Note that instead of correcting the transducer arrangement data directly, the transducer arrangement data may be stored and held separately in the form of difference values or the like relative to transducer arrangement data set in the mechanical design. In this case, the control processor 109 or the image construction unit 112 may perform a correction calculation on the transducer arrangement data in step 501 using these difference values.

According to this configuration of the present invention, variation in the signal reception property of the probe 102, which is configured by disposing a large number of transducers over a substantially spherical crown shape or a substantially spherical zone shape, and in particular variation in the reception property caused by variation in the distances of the transducers 211 from the curvature center point 201, which is a design point set on a mechanical design, can be corrected. Accordingly, a precision with which all of the transducers estimate the position of a sound source is improved, and as a result, high-resolution image data can be generated from the object information.

Furthermore, in this embodiment, simple signal data are acquired using the single point sound source 201, and therefore the signal reception properties of all of the plurality of transducers 211 can be corrected at once.

Note that a comparatively large acoustic wave may be emitted from a member on a surface of the transducer when reflection light from a laser beam reaches the surface of the transducer. When this acoustic wave is detected, the acoustic wave appears on the image as noise. To prevent this noise effectively, a reflective member that does not absorb reflection light may be disposed on the surface of the transducer. Preferred examples of the reflective member include a metallic film or the like exhibiting high reflectance against infrared light.

Further, by performing a correction using actual reception signals, as in this embodiment, elements other than variation in the physical positions of the transducers 211 in a radial direction centering on the curvature center point 201 can also be corrected. More specifically, according to this embodiment, variation in a thickness of the member disposed on the surface of the transducer 211, variation in a response characteristic of a signal reception circuit connected to the transducer 211, and so on can also be corrected.

Second Embodiment

A second embodiment of the present invention will now be described. The apparatus itself used in this embodiment is identical to that illustrated in FIG. 1.

In the first embodiment, described above, the radial direction positions of the transducers 211 relative to the curvature center point 201, which is a design point set on the mechanical design of the probe 102, were corrected. The transducer arrangement coordinate system is preferably set in the apparatus so as to match a coordinate system (x, y, z) (referred to hereafter for convenience as a global coordinate system) of a space in which the apparatus is disposed. However, it is not easy to assemble the apparatus while maintaining a perfect match between the coordinate systems. Hence, in this embodiment, a method of correcting an incline of the transducer arrangement coordinate system on the xy plane will be described. The following description focuses on featured parts of this embodiment.

Using FIG. 8, a flow of a transducer arrangement data correction method according to the second embodiment will be described.

In step 800, similarly to FIG. 7, the point sound source 701 is disposed in the curvature center point 201 of the probe 102, i.e. the origin of the two-dimensional position control performed by the position control mechanism 104. Note that the acoustic transmission medium 711 having a known, stable acoustic velocity property is disposed on the upper portion of the holder 121 at the same time as the point sound source 701 is disposed.

In step 801, the control processor 109 generates control information required to acquire signal data used to correct the transducer arrangement data. As will be described below, movement control information is generated at least twice in relation to position control of the probe 102. Further, when a light absorber that emits a photoacoustic wave is used as the point sound source 701, control information for emitting the light 131 at least twice is generated.

Figure 9A:
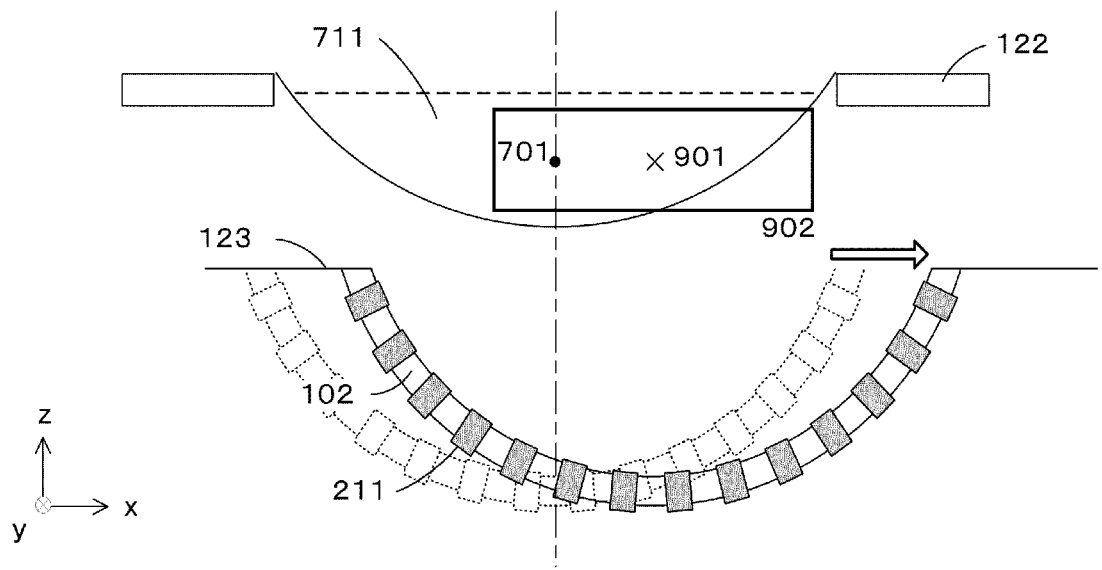
FIGS. 9A and 9B are schematic views showing acquisition of signal data used to calculate a correction amount, according to the second embodiment.

In step 802, as shown in FIG. 9A, the position control mechanism 104 moves the position of the probe 102 by a predetermined distance in a positive direction from the origin along a Px axis of a position control axis. Note that in FIG. 9A, the probe 102 is shown in an origin position of the two-dimensional position control by a dotted outline.

In step 803, the probe 102 detects the propagating acoustic wave emitted by the point sound source 701. Further, the signal reception unit 107 starts to convert the reception signal output from the probe 102 into a digital signal in response to the synchronization signal input from the irradiation optical system 106 or the ultrasonic wave transmission source. Note that likewise in this embodiment, the point sound source 701 may be either an ultrasonic wave transmission source or a point-form light absorber that emits a photoacoustic wave. When a light absorber is used, the photoacoustic wave generated when the light 131 is emitted onto the light absorber 701 is detected.

In step 804, the control processor 109 applies a filter having an identical center wavelength to the acoustic wave emitted by the point sound source 701 to the signal data acquired in step 803. As a result, signal components other than those of the acoustic wave originating from the point sound source 701 are removed, leading to an improvement in the correction precision.

Further, insteps 801 and 802, signal processing for strengthening the signal components originating from the point sound source 701 may be performed by implementing control such that acoustic wave emission from the point sound source and acquisition of the signal data are performed a plurality of times in a single signal data acquisition position and the plurality of acquired signal data are integrated. As a result, the correction precision can be improved.

Figure 10A:
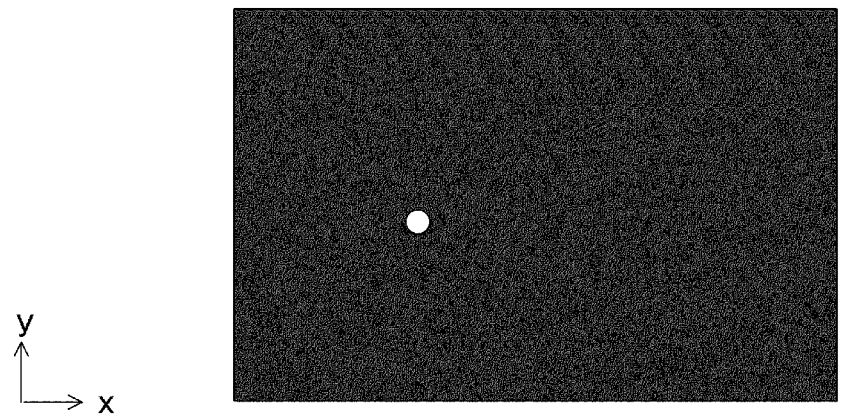
FIGS. 10A to 10C are schematic views showing a point sound source image used to calculate the correction amount, according to the second embodiment.

In step 805, the control processor 109 inputs the signal data acquired up to step 804 and the data attached thereto into the image construction unit 112. The image construction unit 112 then performs reconstruction processing to form an image of the point sound source 701 such as that shown in FIG. 10A. FIG. 10A shows a single xy sectional image of volume data 902 generated for use during the correction, the volume data 902 centering on a position 901 serving as the curvature center point at that time. Note that an image acquired by maximum value projection using a plurality of xy sectional images formed in different z axis positions may be used instead.

In step 806, the control processor 109 determines whether or not images have been acquired in two positions. When images have not been acquired in two positions, the processing advances to step 802, where signal data acquisition and image formation are repeated. When images have been acquired in two positions, the processing advances to step 807.

Figure 9B:
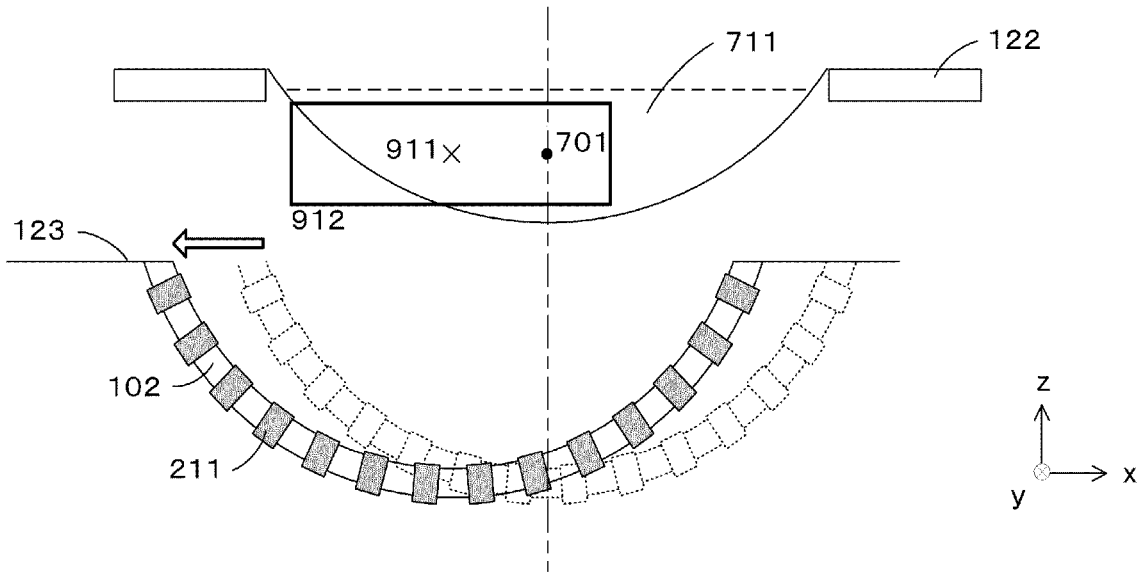
Figure 10B:
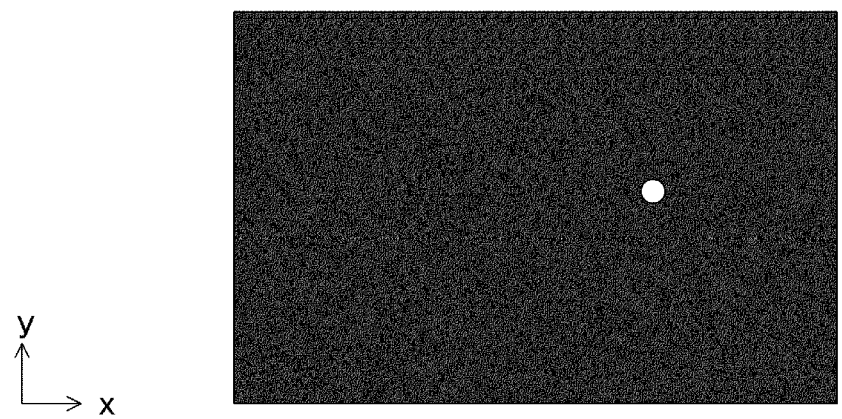
Figure 10C:
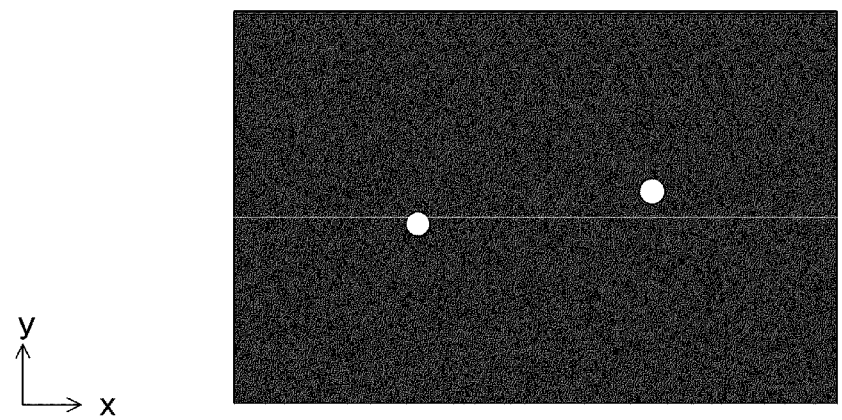

When step 802 is performed for a second time, as shown in FIG. 9B, the position control mechanism 104 moves the position of the probe 102 by an equal distance to an opposite side of the origin. By performing step 803 to step 805 in this second position, an image of the point sound source 701 shown in FIG. 10B can be acquired. FIG. 10B shows a single xy sectional image of volume data 912 generated for use during the correction, the volume data 912 centering on a position 911 serving as the curvature center point at that time. Note that an image acquired by maximum value projection using a plurality of xy sectional images formed in different z axis positions may be used instead.

In step 807, the control processor 109 generates an image shown in FIG. 10O by simply adding together the images shown in FIGS. 10A and 10B, acquired in the steps up to this point, as is without taking into consideration the position control implemented on the probe 102.

In step 808, the control processor 109 calculates coordinates 1101 ($X_L$, $Y_L$), 1102 ($X_R$, $Y_R$) of maximum brightness value positions indicated respectively by the two point sound source images shown in FIG. 100.

Note that here, the position of the probe 102 is controlled only in the x axis direction. Therefore, when the position control axis of the position control mechanism 104 matches the coordinate system in the imaging region, a match is obtained between $Y_L$ and $Y_R$ such that the two images are formed perfectly parallel to each other. When the position control axis is inclined relative to the global coordinate system, on the other hand, the two images are formed such that a straight line linking the two points is inclined, as shown in FIG. 11.

Figure 11:
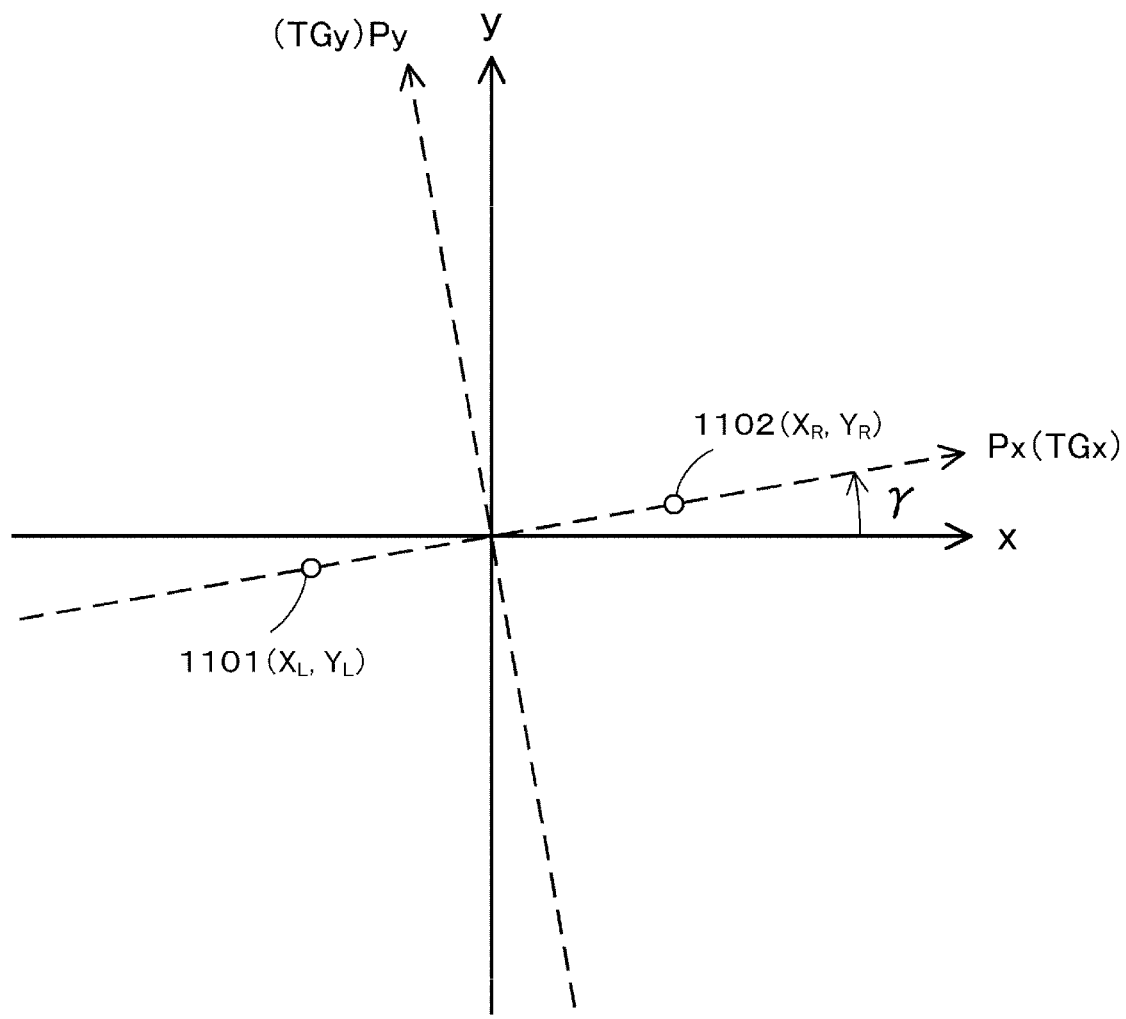
FIG. 11 is a schematic view showing calculation of the correction amount according to the second embodiment.

In step 809, the control processor 109 calculates the incline of the straight line linking the two points, or in other words an angle of deviation γ shown in FIG. 11, as $dx=X_R-X_L$, $dy=Y_R-Y_L$ on the basis of the coordinates of the maximum brightness value positions of the two points, calculated in step 808, using Expression (2).

[Math. 2]

$$\gamma = 2\arctan\frac{dy}{\sqrt{dx^2+dy^2}+dx} \quad (2)$$

In step 810, the control processor 109 stores the correction angle γ calculated in step 809 as correction data. Here, the transducer arrangement data may be updated directly by adding the correction angle γ to the azimuth φ of the transducer arrangement data stored and held in the storage unit 114, or the transducer arrangement data may be stored separately without being updated directly. The stored correction data are referenced in step 501 during the object information visualization flow shown in FIG. 5.

The probe 102 is fixed to the position control mechanism 104 via the connecting portion 241, and therefore rotation of coordinate axes (Px, Py) of the position control mechanism 104 serving as the base of the probe 102 is included in the transducer arrangement coordinate system (TGx, TGy). Hence, in step 501, the transducer positions can be corrected to correct positions in relation to the installed apparatus by referencing the correction data γ and adding or subtracting the correction data γ to or from the azimuth φ of the transducer arrangement data.

Note that the coordinate values of the respective transducers can be converted using the correction angle γ in accordance with Expression (3).

[Math. 3]

$$\begin{pmatrix} TGx' \\ TGy' \\ 1 \end{pmatrix} = \begin{pmatrix} \cos\gamma & \sin\gamma & 0 \\ -\sin\gamma & \cos\gamma & 0 \\ 0 & 0 & 1 \end{pmatrix}\begin{pmatrix} TGx \\ TGy \\ 1 \end{pmatrix} \quad (3)$$

In the example described above, position control in the x axis direction is used as the method of correcting the transducer arrangement data according to this embodiment. However, the correction data γ can be obtained similarly by performing position control in the y axis direction, which is the other axis of the two-dimensional position control performed by the position control mechanism 104.

According to the correction method configured as described above, an incline in the transducer arrangement coordinate axis caused by imprecision in the installation of the position control mechanism 104 can be corrected. As a result, variation in the signal reception property of the probe 102, which is configured by disposing a large number of transducers over a substantially spherical crown shape or a substantially spherical zone shape, can be corrected. In particular, variation in the reception property caused by an incline in the azimuth φ direction on an xy plane having the z axis as a central axis, the incline centering on the curvature center point 201, which is a design point set on the mechanical design, can be corrected favorably.

Moreover, likewise in this embodiment, the signal reception properties of all of the plurality of transducers 211 can be corrected at once by performing simple position control and signal data acquisition operations twice using the single point sound source 201.

Third Embodiment

A third embodiment of the present invention, which uses the apparatus illustrated in FIG. 1 and the correction method of FIG. 8, will now be described.

In the second embodiment, described above, an incline in the azimuth φ direction centering on the curvature center point 201, which is a design point set on the mechanical design of the probe 102, and having the z axis as a central axis was corrected. By evaluating images of two point sound sources on an xz sectional image or a yz sectional image using the volume data acquired in the correction method of FIG. 8, an incline in the transducer arrangement coordinate system having the y axis or the x axis as a central axis can be calculated. In this embodiment, a method of correcting an incline in the transducer arrangement coordinate system (TGx, TGy, TGz) in a polar angle direction relative to the global coordinate system (x, y, z) will be described. The following description focuses on featured parts of this embodiment.

FIG. 12 shows a manner in which signal data are acquired in order to calculate a correction amount to be applied to a probe 1203 in a condition where the probe 1203 is fixed by the connecting portion 241 while inclining in the polar angle direction. This will now be described with reference to the correction flow shown in FIG. 8.

Figure 12A:
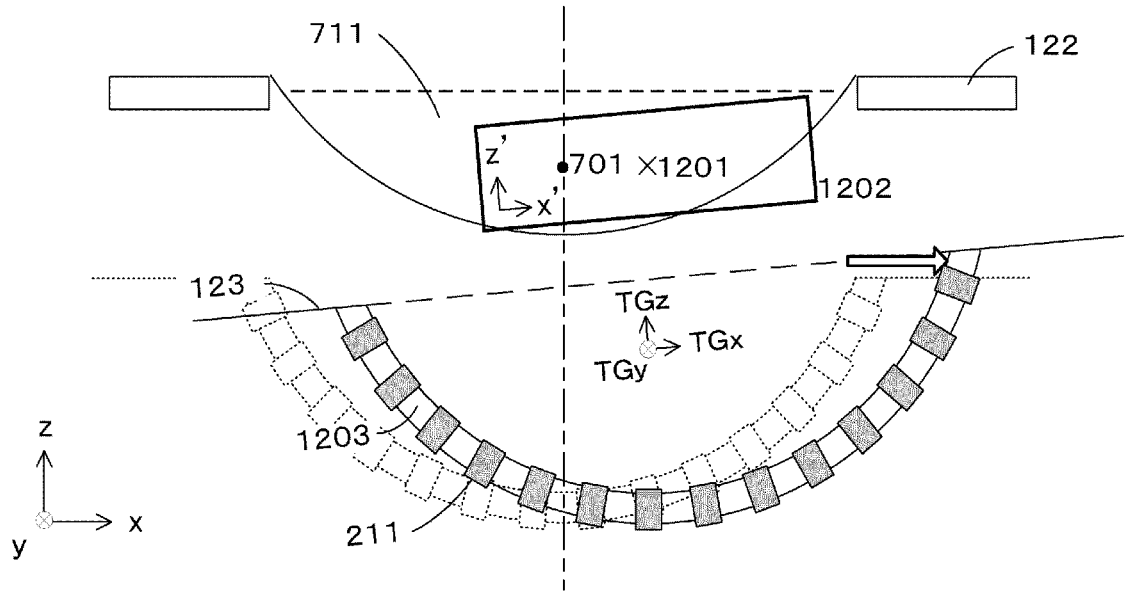
FIGS. 12A and 12B are schematic views showing acquisition of signal data used to calculate a correction amount, according to a third embodiment.

FIG. 12A shows a condition established when the position control mechanism 104 moves the probe 1203 by the predetermined distance in the positive direction from the origin along the Px axis in step 802. When volume data centering on a curvature center point position 1201 are generated in steps 803 to 805, volume data 1202 having a different coordinate system (x', y', z') to the global coordinates (x, y, z) are generated. An incline of this coordinate system (x', y', z') results from the incline in the transducer arrangement coordinate system, and therefore, by calculating this incline, the actual transducer arrangement data can be acquired.

Figure 13A:
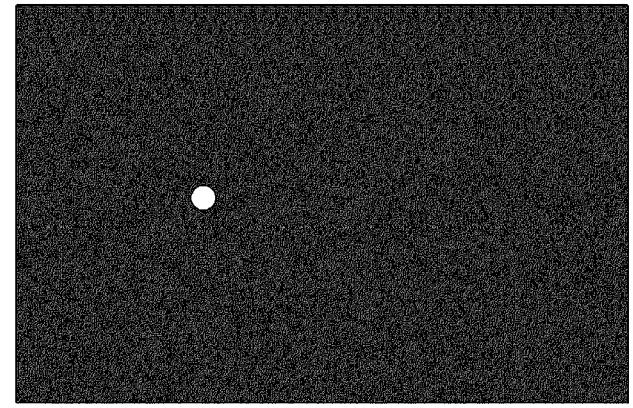
FIGS. 13A to 13C are schematic views showing a point sound source image used to calculate the correction amount, according to the third embodiment.

FIG. 13A shows an x'z' sectional image of the correction volume data 1202, including an image of the point sound source 701. Instead of using a sectional image formed in a single z axis position, an image acquired by maximum value projection using a plurality of xy sectional images formed in different z axis positions may be used.

Figure 12B:
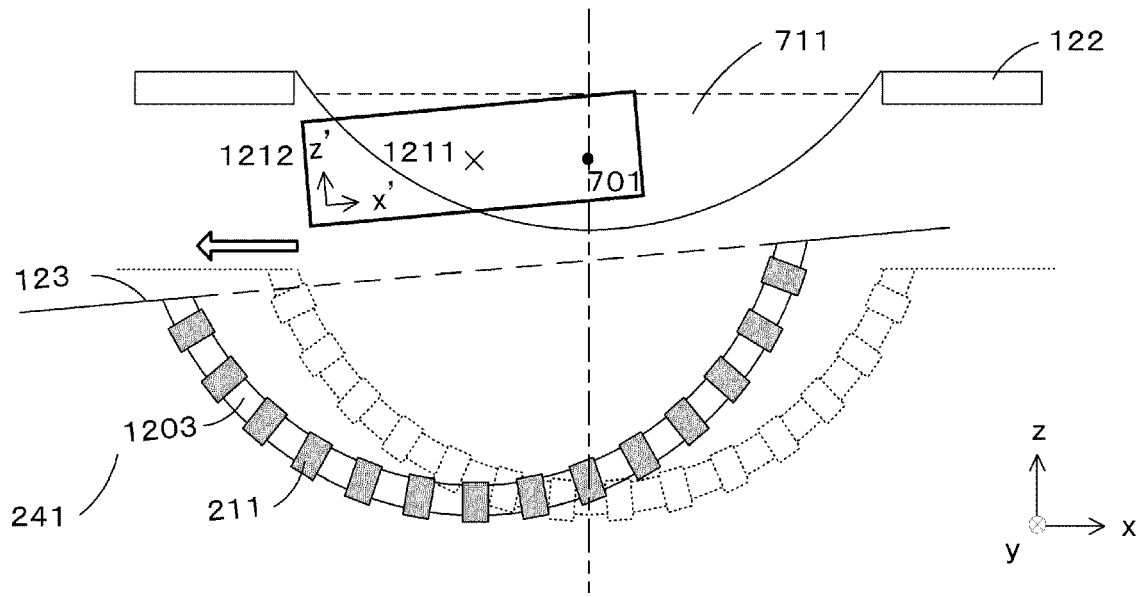
Figure 13B:
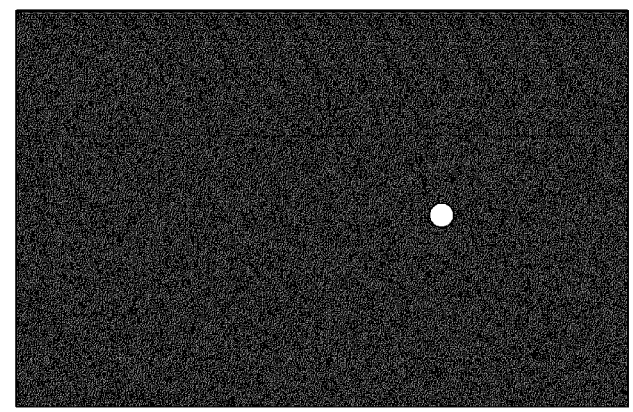

FIG. 12B shows a condition established when the position control mechanism 104 moves the probe 1203 by an equal distance in a negative direction from the origin along the Px axis in step 802 implemented for the second time. By repeating steps 803 to 805 in this probe position, volume data 1212 centering on a curvature center point position 1211 are generated. FIG. 13B shows an x'z' sectional image of the correction volume data 1212, including an image of the point sound source 701. Note that an image acquired by maximum value projection using a plurality of xy sectional images formed in different z axis positions may be used instead.

Figure 13C:
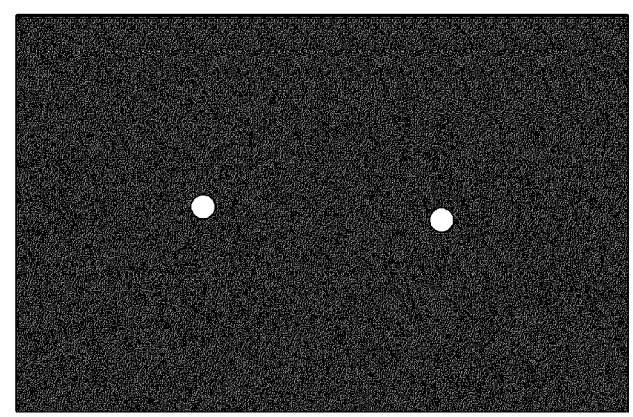

In step 807, an image shown in FIG. 13C is acquired by simply adding together the images shown in FIGS. 13A and 13B, acquired in the steps up to this point, as is without taking into consideration the position control implemented on the probe 102.

In step 808, the control processor 109 calculates coordinates 1401 ($X_L$, $Z_L$), 1402 ($X_R$, $Z_R$) of the maximum brightness value positions indicated respectively by the two point sound source images shown in FIG. 13C. Note that the position of the probe 102 is controlled only in the x axis direction, and therefore, when the image coordinate system (x', y', z'), or in other words the transducer arrangement coordinate system (TGx, TGy, TGz) of the probe 102, matches the global coordinate system (x, y, z), a match is obtained between $Z_L$ and $Z_R$. As a result, the two images are formed perfectly parallel to each other.

Figure 14:
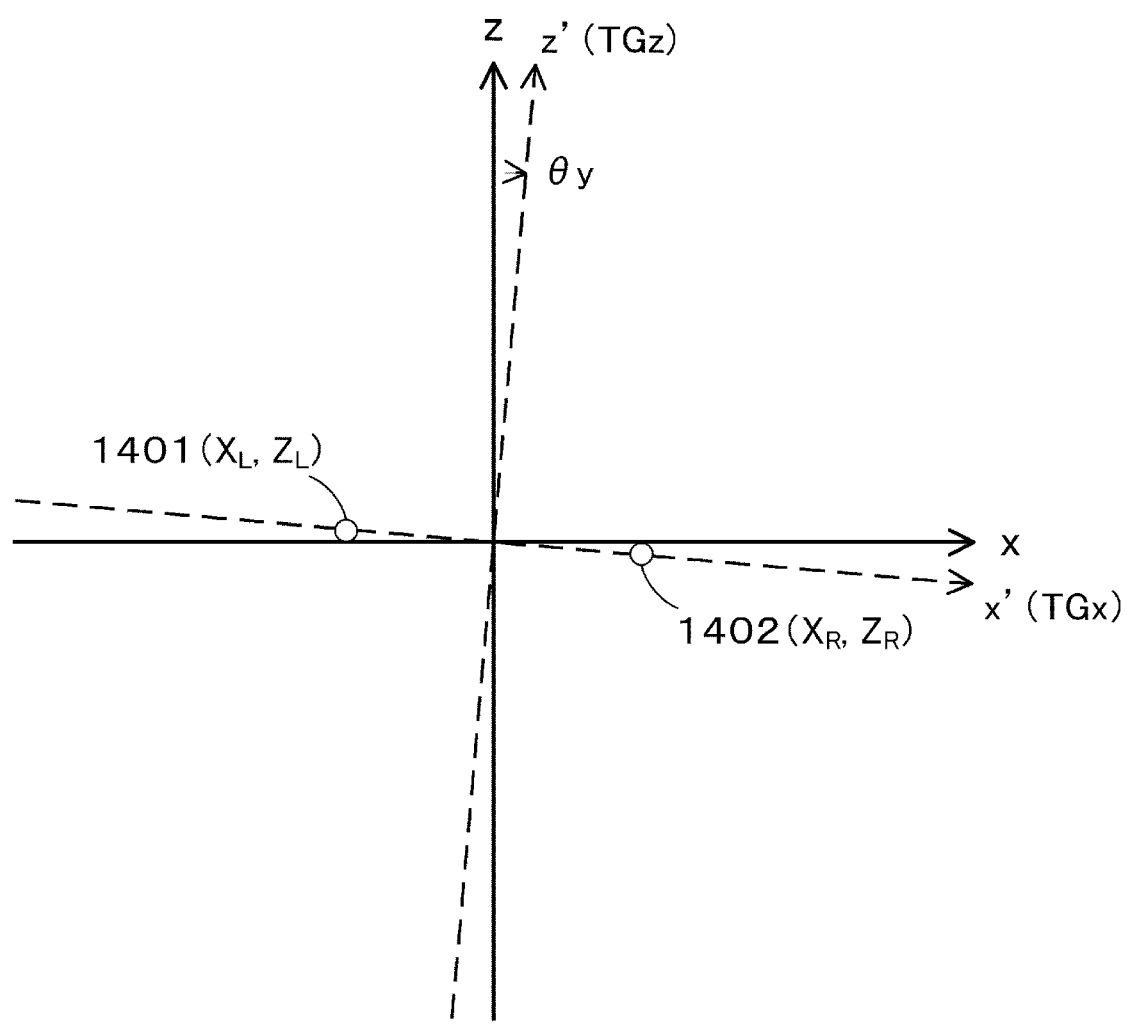
FIG. 14 is a schematic view showing calculation of the correction amount according to the third embodiment.

When the transducer arrangement coordinate system is inclined in the polar angle direction relative to the global coordinate system, on the other hand, the two images are formed such that a straight line linking the two points is inclined, as shown in FIG. 14.

In step 809, the control processor 109 calculates the incline of the straight line linking the two points, or in other words an angle of deviation $\theta_y$ shown in FIG. 14, as $dx = X_R - X_L$, $dy = Y_R - Y_L$ on the basis of the coordinates of the maximum brightness value positions of the two points using Expression (4).

[Math. 4]

$$\theta_x = 2\arctan \frac{dy}{\sqrt{dx^2 + dy^2} + dx} \quad (4)$$

By performing position control on the probe 1203 along the x axis and acquiring images of the point sound source 701 in two different x axis positions relative to the point sound source 701 in this manner, correction data $\theta_y$ for correcting a polar angle direction incline about the y axis are acquired.

By evaluating the incline using a y'z' sectional image, on the other hand, correction data $\theta_y$ for correcting a polar angle direction incline about the x axis are acquired similarly using Expression (5).

[Math. 5]

$$\theta_y = 2\arctan \frac{dy}{\sqrt{dx^2 + dy^2} + dx} \quad (5)$$

Here, $Y_R$ and $Y_L$ denote the positions of the two images of the point sound source 701 on the y'z' sectional image.

Note that the actual incline is constituted by a combination of $\theta_x$ and $\theta_y$, and therefore, to improve the calculation precision of the respective components, the incline may be calculated by performing position control on the probe 1203 in the y axis direction in addition to the position control performed along the x axis.

In step 810, the control processor 109 stores the correction angles $\theta_x$ and $\theta_y$ calculated in step 809 as correction data. The correction data stored here are referenced in step 501 during the object information visualization flow shown in FIG. 5.

On the basis of the correction data $\theta_x$ and $\theta_y$ serving as the two components of the incline in the polar angle direction, a rotation angle $\alpha$ in the azimuth $\phi$ direction having the z axis as a central axis and a new rotation angle $\beta$ in the polar angle $\theta$ direction centering on the x axis, which is acquired as a result of a rotation by the angle $\alpha$, can be calculated. Using these angles and the correction data $\gamma$ calculated in the second embodiment, the transducer arrangement data can be corrected in step 501 in accordance with Expression (6).

[Math. 6]

$$\begin{pmatrix} TGx' \\ TGy' \\ TGz' \\ 1 \end{pmatrix} = \begin{pmatrix} \cos\gamma & \sin\gamma & 0 & 0 \\ -\sin\gamma & \cos\gamma & 0 & 0 \\ 0 & 0 & 1 & 0 \\ 0 & 0 & 0 & 1 \end{pmatrix} \begin{pmatrix} 1 & 0 & 0 & 0 \\ 0 & \cos\beta & \sin\beta & 0 \\ 0 & -\sin\beta & \cos\beta & 0 \\ 0 & 0 & 0 & 1 \end{pmatrix} \quad (6)$$

$$\begin{pmatrix} \cos\alpha & \sin\alpha & 0 & 0 \\ -\sin\alpha & \cos\alpha & 0 & 0 \\ 0 & 0 & 1 & 0 \\ 0 & 0 & 0 & 1 \end{pmatrix} \begin{pmatrix} TGx \\ TGy \\ TGz \\ 1 \end{pmatrix}$$

$$= \begin{pmatrix} \cos\alpha\cos\beta\cos\gamma - \sin\alpha\sin\gamma & -\cos\alpha\cos\beta\sin\gamma - \sin\alpha\cos\gamma & \cos\alpha\sin\beta & 0 \\ \sin\alpha\cos\beta\cos\gamma + \cos\alpha\sin\gamma & -\sin\alpha\cos\beta\sin\gamma + \cos\alpha\cos\gamma & \sin\alpha\sin\beta & 0 \\ -\sin\beta\cos\gamma & \sin\beta\sin\gamma & \cos\beta & 0 \\ 0 & 0 & 0 & 1 \end{pmatrix} \begin{pmatrix} TGx \\ TGy \\ TGz \\ 1 \end{pmatrix}$$

According to this configuration of the present invention, an incline in the transducer arrangement coordinate system of the probe 102 due to imprecision in the installation of the probe 102 on the position control mechanism 104 in the apparatus can be corrected. In other words, [variation in] the signal reception property of the probe 102, which is configured by disposing a large number of transducers over a substantially spherical crown shape or a substantially spherical zone shape, can be corrected. In particular, [variation in] the reception property caused by an incline in the polar angle $\theta$ direction centering on the curvature center point 201, which is a design point set on the mechanical design, can be corrected favorably.

Moreover, likewise in this embodiment, the signal reception properties of all of the plurality of transducers 211 can be corrected at once by performing simple position control and signal data acquisition operations twice using the single point sound source 201.

Fourth Embodiment

A modified example of the third embodiment will now be described. In the third embodiment, described above, the correction data $\theta_x$ and $\theta_y$ relating to the polar angle direction were acquired by controlling the position of the probe 1203 along the control axis of the position control mechanism 104 relative to the single point sound source 701 in order to acquire two images. In this embodiment, a fully equivalent effect is obtained by a single image acquisition operation, i.e. without controlling the position of the probe 1203, using at least two point sound sources, positions of which are managed with a high degree of precision.

Figure 15:
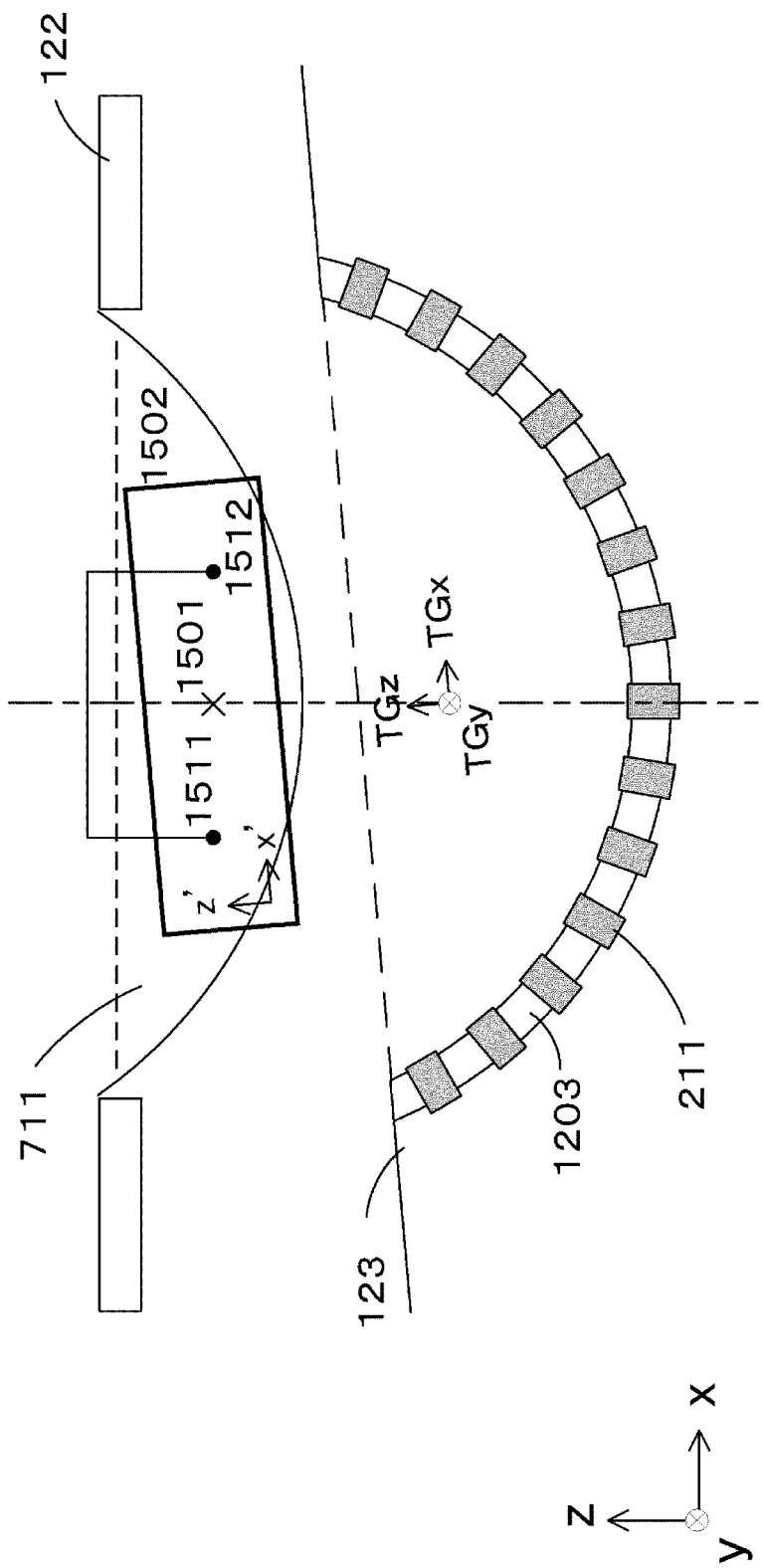
FIG. 15 is a schematic view showing acquisition of signal data used to calculate a correction amount, according to a fourth embodiment.

FIG. 15 shows signal data acquisition for calculating a correction amount according to the fourth embodiment. Two point sound sources 1511 and 1512, positions of which are managed with a high degree of precision using a mechanical support, are disposed in the x axis direction about a curvature center point 1501 of the probe 1203.

In steps 803 to 805, an identical image to that of FIG. 13C can be generated by detecting acoustic waves emitted from the two point sound sources 1511 and 1512 so as to acquire the signal data all at once. Hence, the correction data $\theta_y$ relating to a polar angle direction incline having the y axis as a center axis and the incline correction data $\theta_x$ having the x axis as a center axis can be acquired in a single process, i.e. without repeating the signal data acquisition and imaging processes a plurality of times in accordance with the position control.

Note that the actual incline is constituted by a combination of $\theta_x$ and $\theta_y$, and therefore, to improve the calculation precision of the respective components, the incline may be calculated by disposing point sound sources along the y axis direction in addition to the point sound sources disposed along the x axis so as to acquire the signal data in a similar manner.

A configuration in which four point sound sources constituted by orthogonally disposed combinations of two point sound sources may also be employed.

With the correction method having the configuration described above, [variation in] the signal reception properties of all of the plurality of transducers 211 due to an incline in the polar angle direction can be corrected at once by performing simple position control and signal data acquisition operations once using at least two point sound sources, positions of which are managed with a high degree of precision.

Fifth Embodiment

A fifth embodiment of the present invention, which uses the apparatus illustrated in FIG. 1, will now be described.

The embodiments described heretofore respectively provide methods of correcting the positions of the transducers relative to an incline centering on the curvature center point 201, which is a design point set on the mechanical design of the probe 102, and having the radial direction and the respective axes of the transducer arrangement coordinate system as a central axis. In this embodiment, a method of measuring the positions of the plurality of transducers 211 on the global coordinate system will be described. The following description focuses on featured parts of this embodiment.

Figure 8:
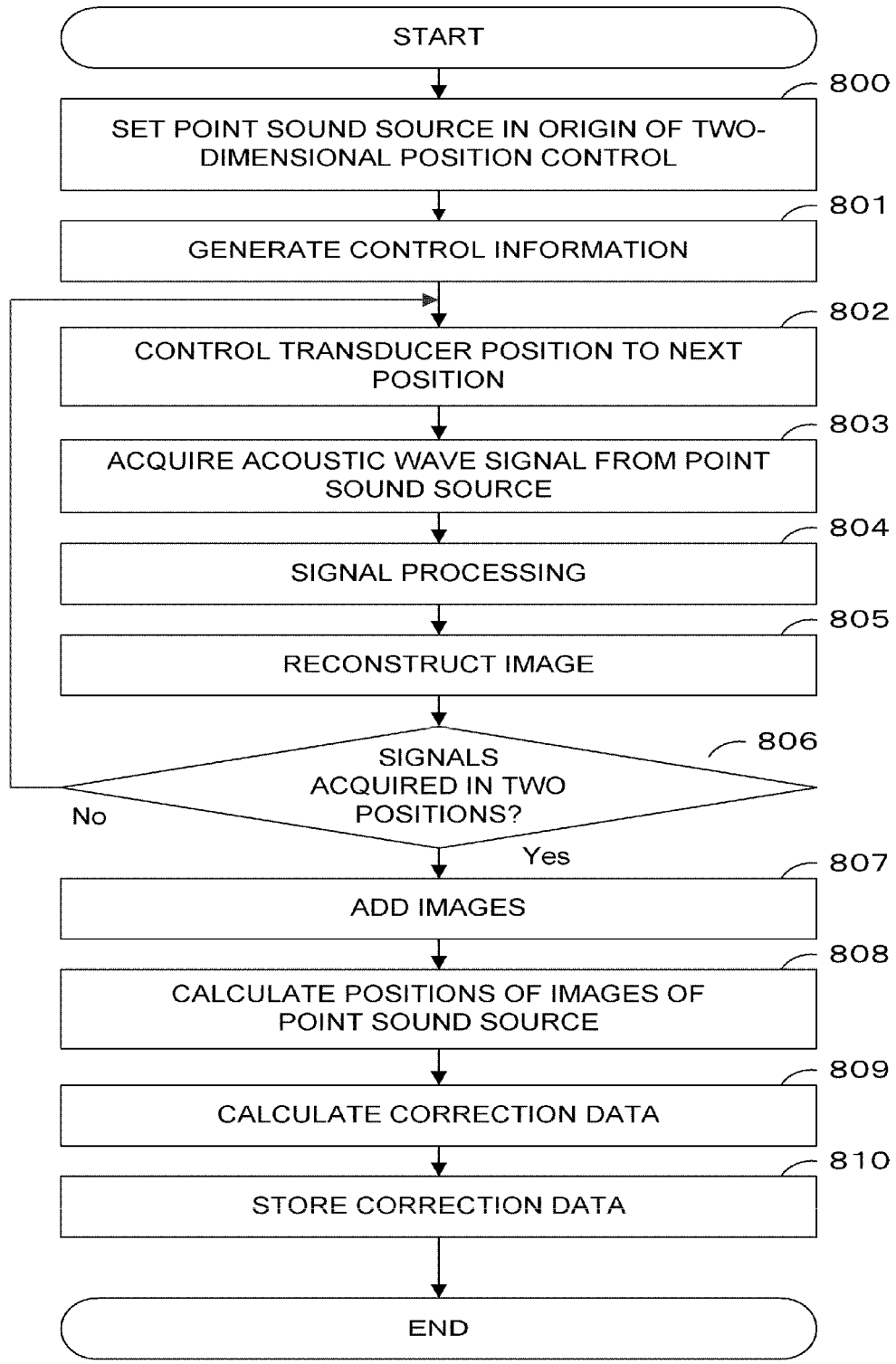
FIG. 8 is a flowchart showing correction according to a second embodiment.

Note that the method of correcting the transducer arrangement data according to the fifth embodiment can be implemented simply by partially modifying the flow of the second embodiment, shown in FIG. 8.

More specifically, in step 801, the control processor 109 generates control information for acquiring signal data in at least three positions. Then, in step 806, the control processor 109 determines whether or not images have been acquired in at least three positions. When images have not been acquired in three positions, the processing advances to step 802, where signal data acquisition and imaging are repeated. When images have been acquired in three positions, the processing advances to step 807.

Referring to FIG. 16, acquisition of the signal data used to calculate the correction amount according to the fifth embodiment will be described. This will be described with reference to the correction flow shown in FIG. 8.

In step 800, similarly to FIG. 7, the point sound source 701 is disposed in the curvature center point 201 of the probe 102, which is disposed at an origin of three-dimensional position control performed by the position control mechanism 104. Note that the acoustic transmission medium 711 having a known, stable acoustic velocity property is disposed on the upper portion of the holder 121 at the same time as the point sound source 701 is disposed.

In step 801, the control processor 109 generates movement control information at least three times in relation to position control of the probe 102, and when a light absorber that emits a photoacoustic wave is used as the point sound source 701, generates control information for emitting the light 131 at least three times.

Figure 16A:
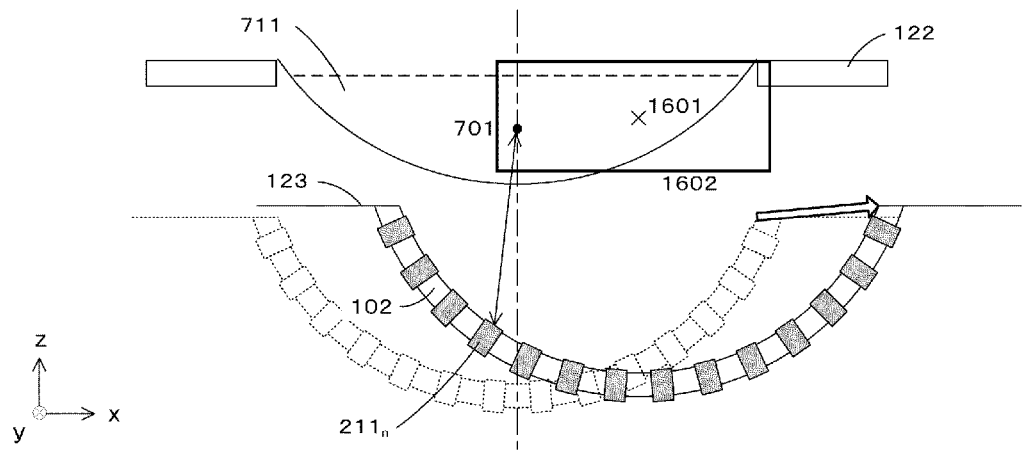
FIGS. 16A to 16C are schematic views showing acquisition of signal data used to calculate a correction amount, according to a fifth embodiment.
Figure 16B:
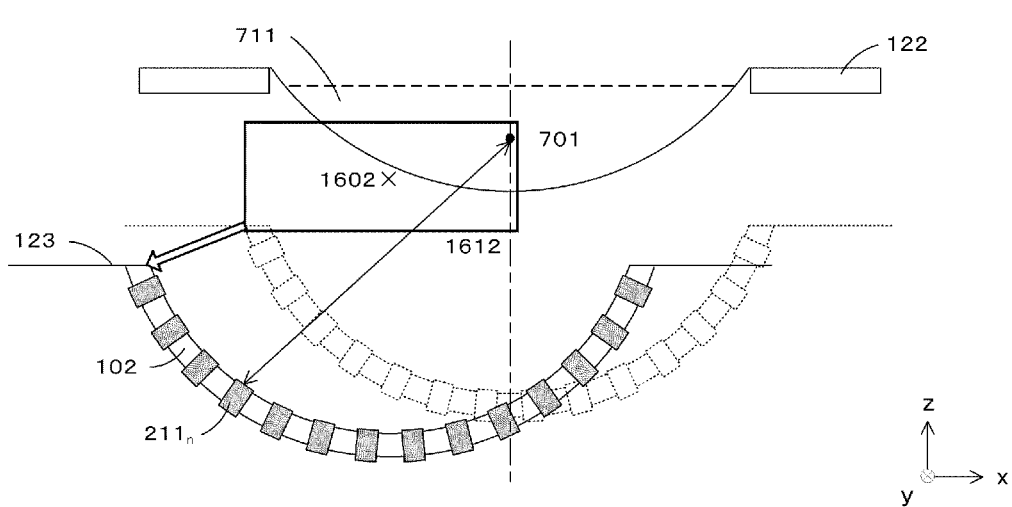
Figure 16C:
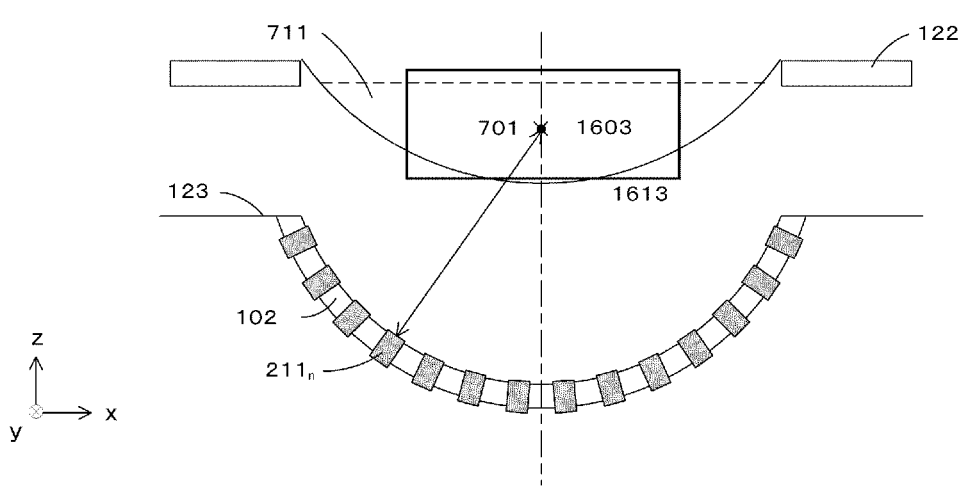

In step 802, which is implemented three times, the position control mechanism 104 moves the position of the probe 102 respectively to a first position shown in FIG. 16A, a second position shown in FIG. 16B, and a third position shown in FIG. 16C. Note that in FIG. 16, an origin position of the probe 102 during the three-dimensional position control is indicated by a dotted outline.

Figure 17A:
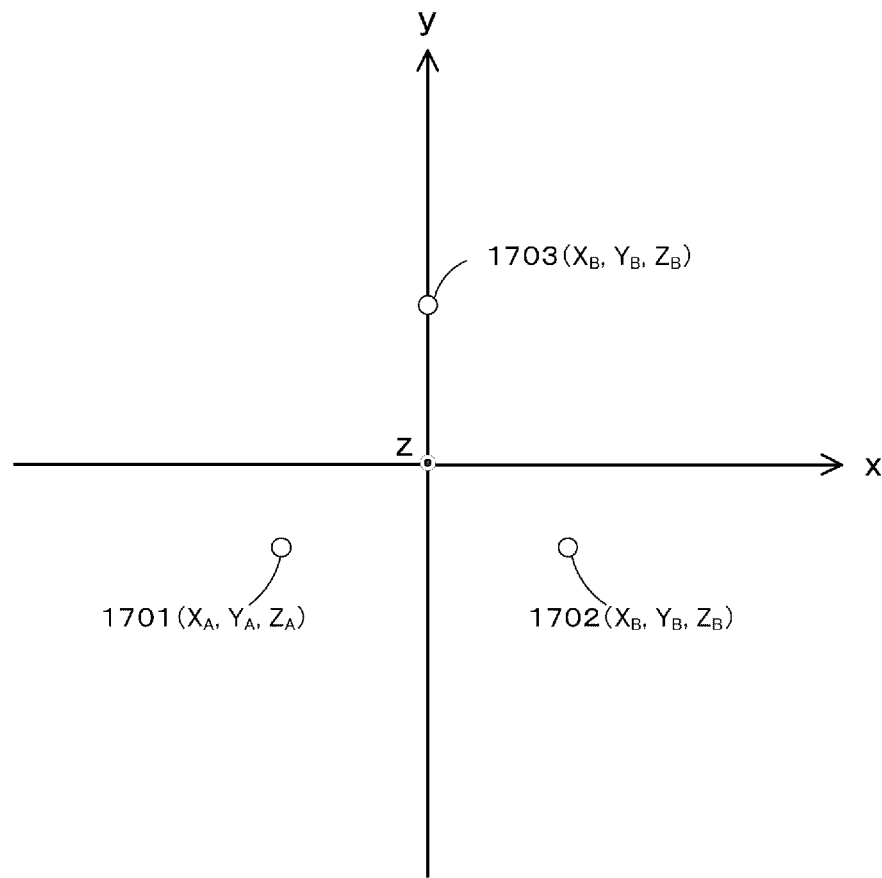
FIGS. 17A and 17B are schematic views showing calculation of the correction amount according to the fifth embodiment.
Figure 17B:
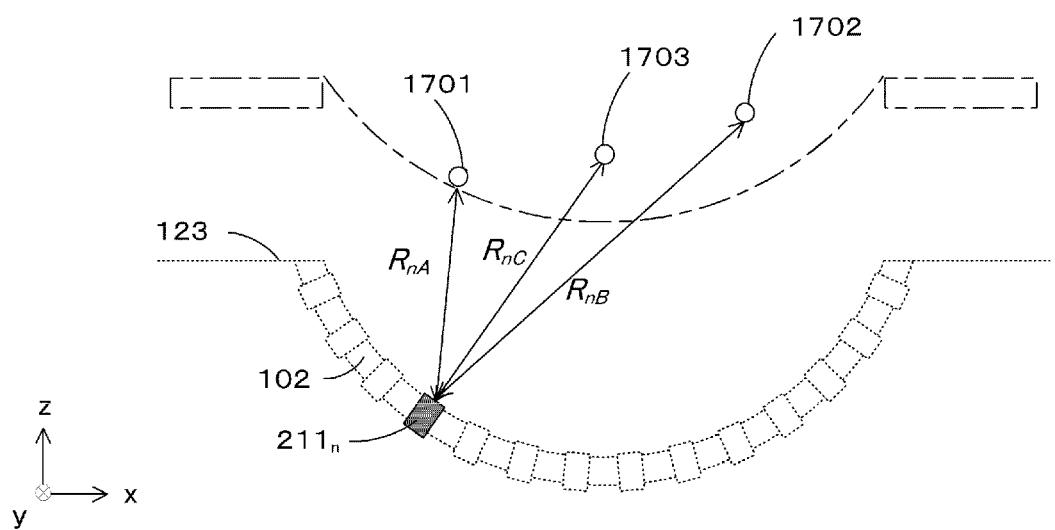

FIGS. 17A and 17B show images of the three point sound sources, which are acquired through the processing of steps 802 to 807. In step 808, the control processor 109 calculates coordinates 1701 $(X_A, Y_A, Z_A)$, 1702 $(X_B, Y_B, Z_B)$ 1703 $(X_C, Y_C, Z_C)$ of maximum brightness value positions of the respective images. A three-dimensional position $(X_n, Y_n, Z_n)$ of the transducer 211$_n$ can then be calculated from the coordinates of the maximum brightness value positions of the three points using Expression (7).

[Math. 7]

$$(X_M - x_n)^2 + (Y_M - y_n)^2 + (Z_M - z_n)^2 = R_{nM}^2 = c^2 T_{nM}^2 \approx c^2 \frac{S_{nM}^2}{F^2} \quad (7)$$

$$M = A, B, C, \ldots$$

Here, M denotes a sign of the respective coordinates of A, B, and C, c denotes the acoustic velocity of the acoustic wave through the acoustic transmission medium, $R_{nM}$ denotes the distances from the respective transducers 211$_n$ to the point sound source 701, $T_{nM}$ denotes reception times of the respective acoustic waves, and $S_{nM}$ denotes the sampling positions of the respective acoustic wave signals. Note that a positional relationship between the coordinates 1701, 1702, and 1703 is already known from the position control amounts applied by the position control mechanism 104.

In step 810, the control processor 109 updates the transducer arrangement data using the measured transducer positions of all of the transducers.

Note that in this embodiment, images of the point sound source 701 are acquired in three relative positions, whereupon the three-dimensional positions of the respective transducers are measured from these images. At this time, the three images of the point sound source are positioned on a single plane linking the images. When the plurality of transducers 211 are disposed on a substantially spherical crown shape or a substantially spherical zone shape, the plurality of transducers disposed around substantially an entire circumference in the azimuth ϕ direction observe the three point sound sources. Depending on the position of the transducer, therefore, the point sound sources may overlap or approach each other, leading to a reduction in measurement precision. To improve the measurement precision, therefore, it is effective to perform the measurement using a larger number of point sound source images.

According to the correction method having the above configuration, the position of the probe 102 configured by disposing a large number of transducers over a substantially spherical crown shape or a substantially spherical zone shape can be measured. Furthermore, likewise in this embodiment, the three-dimensional positions of all of the plurality of transducers 211 can be corrected at once by performing simple position control and signal data acquisition operations up to three times using the single point sound source 701.

Sixth Embodiment

A modified example of the fifth embodiment will now be described. In the fifth embodiment, the three-dimensional positions of the plurality of transducers 211 were measured by subjecting the probe 102 to three-dimensional position control relative to the single point sound source 701, using the position control mechanism 104 in order to acquire at least three images. However, position control does not necessarily have to be performed on the probe in order to determine the positions of the transducers.

More specifically, in this embodiment, at least three point sound sources, positions of which are managed with a high degree of precision, are used so that images of the three point sound sources are acquired all at once without controlling the position of the probe. As a result, similar effects to the fifth embodiment are acquired.

Seventh Embodiment

Needless to mention, the object of the present invention may also be achieved as follows. A storage medium (or a recording medium) storing software program code with which to realize the functions of the embodiments described above is supplied to a system or an apparatus. A computer (or a CPU or MPU) of the system or the apparatus reads and executes the program code stored on the storage medium. In this case, the functions of the embodiments described above are realized by the program code read from the storage medium, while the storage medium storing the program code constitutes the present invention.

Further, when the computer executes the read program code, an operating system (OS) or the like operating on the computer performs all or a part of the actual processing on the basis of instructions included in the program code. A case in which the functions of the embodiments described above are realized by this processing is also included in the scope of the present invention.

Furthermore, the program code read from the storage medium may be written to a memory provided in a function expansion card inserted into the computer or a function expansion unit connected to the computer. A CPU or the like provided in the function expansion card or the function expansion unit then performs all or a part of the actual processing on the basis of the instructions included in the program code. A case in which the functions of the embodiments described above are realized by this processing is also included in the scope of the present invention.

When the present invention is applied to this type of storage medium, program code corresponding to the flowcharts described above is stored on the storage medium.

Persons skilled in the art will find no difficulty in configuring a new system by appropriately combining the various techniques described in the above embodiments, and therefore systems obtained as a result of these various combinations also belong to the scope of the present invention.

OTHER EMBODIMENTS

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of U.S. Provisional Application No. 62/046,339, filed on Sep. 5, 2014, which is hereby incorporated by reference herein in its entirety.

What is claimed is:

1. An object information acquiring apparatus comprising:
   a plurality of transducers that respectively generate electric signals upon reception of an acoustic wave from a measurement subject;
   a supporter that supports the plurality of transducers such that directional axes of at least a part of the plurality of transducers are gathered together;
   a position controller that controls a relative position of the measurement subject and the supporter;
   a memory storing a program; and
   one or more processors which, by executing the program, causes the object information acquiring apparatus to:
      determine respective distances from each of the plurality of transducers to a focus position of the measurement subject, on the basis of information indicating respective positions of the plurality of transducers in the relative position,
      generate property information relating to the focus position of the measurement subject by performing image reconstruction processing on the electric signals, using the respective distances, and
      determine correction data for the information indicating the respective positions of the plurality of transducers in the relative position, using a synthesized image obtained by synthesizing a first image and a second image of the measurement subject acquired respectively in at least two relative positions, wherein the first image includes a first point, the second image includes a second point, the synthesized image includes the first point and the second point, and the correction data is determined using a positional relationship of the first point and the second point in the synthesized image, and wherein the property information is generated by further performing image reconstruction processing on the electric signals using the correction data.

2. The object information acquiring apparatus according to claim 1, wherein the measurement subject is an object constituted by a living organism or a phantom, and one of the processors corrects the information indicating respective positions of the plurality of transducers, using the correction data while generating property information relating to an interior of the object.

3. The object information acquiring apparatus according to claim 1, wherein the supporter supports the plurality of transducers such that the directional axes of the plurality of transducers form a high sensitivity region.

4. The object information acquiring apparatus according to claim 3, wherein the position controller controls the supporter such that the high sensitivity region overlaps the focus position.

5. The object information acquiring apparatus according to claim 1, wherein the supporter has a substantially spherical crown shape or a substantially spherical zone shape, and the focus position is set in a curvature center of the supporter.

6. The object information acquiring apparatus according to claim 1, wherein the one or more processors further cause the object information acquiring apparatus to determine correction data for correcting information indicating the positions of at least a part of the plurality of transducers relative to a design point set on a mechanical design of the supporter.

7. The object information acquiring apparatus according to claim 1, wherein the plurality of transducers receive the acoustic wave propagating from the focus position in the relative position controlled by the position controller, and one of the processors generates the images of the measurement subject on the basis of the acoustic wave deriving from the focus position acquired in the relative position.

8. The object information acquiring apparatus according to claim 7, wherein the one or more processors further cause the object information acquiring apparatus to determine correction data for correcting an incline in the plurality of transducers, using the synthesized image.

9. The object information acquiring apparatus according to claim 1, further comprising a light source, wherein the focus position is an absorber that emits an acoustic wave upon reception of light from the light source.

10. An object information acquiring method comprising the steps of:

generating electric signals upon reception of an acoustic wave from a measurement subject with each of a plurality of transducers which are supported by a supporter that supports the plurality of transducers such that directional axes of at least a part of the plurality of transducers are gathered together;

controlling a relative position of the measurement subject and the supporter with a position controller;

determining, with a processor, respective distances from each of the plurality of transducers to a focus position of the measurement subject on the basis of information indicating respective positions of the plurality of transducers in the relative position, generating, with the processor, property information relating to the focus position of the measurement subject by performing image reconstruction processing on the electric signals using the respective distances; and determining correction data for the information indicating the respective positions of the plurality of transducers in the relative position, using a synthesized image obtained by synthesizing a first image and a second image of the measurement subject acquired respectively in at least two relative positions, wherein the first image includes a first point, the second image includes a second point, the synthesized image includes the first point and the second point, and the correction data is determined using a positional relationship of the first point and the second point in the synthesized image, and wherein the property information is generated by further performing image reconstruction processing on the electric signals using the correction data.

11. The object information acquiring method according to claim 10, wherein the measurement subject is an object constituted by a living organism or a phantom, and further comprising:

correcting the information indicating the respective positions of the plurality of transducers, using the correction data determined in the determining step of the correction data while generating property information relating to an interior of the object with the processor.

12. The object information acquiring method according to claim 10, wherein the supporter supports the plurality of transducers such that the directional axes of the plurality of transducers form a high sensitivity region.

13. The object information acquiring method according to claim 12, wherein in the controlling step, the supporter is controlled with the position controller such that the high sensitivity region overlaps the focus position.

14. The object information acquiring method according to claim 10, wherein the supporter has a substantially spherical crown shape or a substantially spherical zone shape, and the focus position is set in a curvature center of the supporter.

15. The object information acquiring method according to claim 10, wherein in the determining step of the correction data, the correction data is determined for correcting information indicating the positions of at least a part of the plurality of transducers relative to a design point set on a mechanical design of the supporter.

16. The object information acquiring method according to claim 10, wherein in the generating step, the acoustic wave propagating from the focus position is received in the relative position controlled in the controlling step with the plurality of transducers, further comprising a step of generating the images of the measurement subject on the basis of the acoustic wave deriving from the focus position acquired in the relative position with the processor.

17. The object information acquiring method according to claim 16, wherein in the determining step of correction data, the correction data is determined for correcting an incline in the plurality of transducers, using the synthesized image.

18. The object information acquiring method according to claim 10, wherein the focus position is an absorber that emits an acoustic wave upon reception of light from a light source.

19. The object information acquiring apparatus according to claim 1, wherein the one or more processors further cause the object information acquiring apparatus to determine correction data for the information indicating the respective positions of the plurality of transducers, using respective reception times at which the acoustic wave from the focus position is received in the plurality of transducers and an acoustic velocity on a path of the acoustic wave.

20. The object information acquiring method according to claim 10, further comprising determining correction data for the information indicating the respective positions of the plurality of transducers, using respective reception times at which the acoustic wave from the focus position is received in the plurality of transducers and an acoustic velocity on a path of the acoustic wave.

21. An object information acquiring apparatus comprising:
   a plurality of transducers that respectively generate electric signals upon reception of an acoustic wave from a measurement subject;
   a supporter that supports the plurality of transducers such that directional axes of at least a part of the plurality of transducers are gathered together;
   a position controller that controls a relative position of the measurement subject and the supporter;
   a memory storing a program; and
   one or more processors which, by executing the program, causes the object information acquiring apparatus to:
      determine respective distances from each of the plurality of transducers to a focus position of the measurement subject, on the basis of information indicating respective positions of the plurality of transducers in the relative position,
      generate property information relating to the focus position of the measurement subject, by performing image reconstruction processing on the electric signals, using the respective distances;
      determine correction data for the information indicating the respective positions of the plurality of transducers in the relative position, using a synthesized image obtained by synthesizing images of the measurement subject acquired respectively in the relative position, and
      determine correction data for correcting an incline in the plurality of transducers, using the synthesized image.

* * * * *